(12) United States Patent
Iversen et al.

(10) Patent No.: US 10,538,769 B2
(45) Date of Patent: Jan. 21, 2020

(54) RENAL SELECTIVE INHIBITION OF CYTOCHROME P450 3A5

(71) Applicant: Oregon State University, Corvallis, OR (US)

(72) Inventors: Patrick L. Iversen, Corvallis, OR (US); Andrew J. Annalora, Corvallis, OR (US)

(73) Assignee: Oregon State University, Corvallis, OR (US)

( * ) Notice: Subject to any disclaimer, the term of this patent is extended or adjusted under 35 U.S.C. 154(b) by 0 days.

(21) Appl. No.: 15/757,192

(22) PCT Filed: Sep. 2, 2016

(86) PCT No.: PCT/US2016/050239
§ 371 (c)(1),
(2) Date: Mar. 2, 2018

(87) PCT Pub. No.: WO2017/041020
PCT Pub. Date: Mar. 9, 2017

(65) Prior Publication Data
US 2018/0258433 A1  Sep. 13, 2018

Related U.S. Application Data

(60) Provisional application No. 62/214,279, filed on Sep. 4, 2015.

(51) Int. Cl.
*C12N 15/113* (2010.01)
*A61K 31/712* (2006.01)
*C07K 14/80* (2006.01)

(52) U.S. Cl.
CPC ...... *C12N 15/1137* (2013.01); *C12N 2310/11* (2013.01); *C12N 2310/314* (2013.01); *C12N 2310/321* (2013.01); *C12N 2310/3233* (2013.01)

(58) Field of Classification Search
CPC ............ C12N 15/1137; A01K 2207/05; A61K 31/712
See application file for complete search history.

(56) References Cited

U.S. PATENT DOCUMENTS

| | | | |
|---|---|---|---|
| 6,673,778 B1 | 1/2004 | Iversen | |
| 6,686,338 B1 | 2/2004 | Iversen | |
| 7,022,475 B2 | 4/2006 | Schuetz et al. | |
| 8,198,429 B2 | 6/2012 | Iversen et al. | |
| 2004/0229829 A1 | 11/2004 | Iversen | |
| 2006/0122133 A1* | 6/2006 | Weinstein | C12N 15/1136 514/44 A |
| 2008/0050718 A1* | 2/2008 | Gesteland | G06F 19/20 435/5 |
| 2009/0241204 A1 | 9/2009 | Daly | |
| 2013/0344135 A1 | 12/2013 | van Rooij et al. | |

FOREIGN PATENT DOCUMENTS

| | | |
|---|---|---|
| WO | WO 2001/87286 | 11/2001 |
| WO | WO 2007/064853 | 6/2007 |
| WO | WO 2008/033432 | 3/2008 |

OTHER PUBLICATIONS

Ho et al. Hypertension 45: 294-298 (Year: 2005).*
Zhang et al. Journal of Human Hypertension 28, pp. 145-149 (Year: 2014).*
Fisher et al. Journal of Human Hypertension 30, pp. 778-782 (Year: 2016).*
Arora et al., "Phosphorodiamidate Morpholino Antisense Oligomers Inhibit Expression of Human Cytochrome P450 3A4 and Alter Selected Drug Metabolism," *Drug Metab. Dispos.*, vol. 30:757-762, 2002.
Desjardins and Iversen, "Inhibition of the Rat Cytochrome P450 3A2 by an Antisense Phosphorothioate Oligodeoxynucleotide In Vivo," *J. Pharmacol. Exp. Ther.*, vol. 275:1608-1613, 1995.
Ferraresso et al., "Association between CYP3A5 polymorphisms and blood pressure in kidney transplant recipients receiving calcineurin inhibitors," *Clin Exp Hypertens* 33(6): 359-365, 2011.
Givens et al., "CYP3A5 genotype predicts renal CYP3A activity and blood pressure in healthy adults," *J Appl Phys* 95: 1297-1300, 2003.
Geary et al., "Pharmacokinetics, biodistribution and cell uptake of antisense oligonucleotides," *Adv Drug Deliv Rev*. 87:46-51, 2015.
Ghosh et al., "Renal and Hepatic Family 3A Cytochromes P450 (CYP3A) in Spontaneously Hypertensive Rats," *Biochem Pharmacol* 50(1): 49-54, 1995.
Lin et al., "Co-Regulation of CYP3A4 and CYP3A5 and Contribution to Hepatic and Intestinal Midazolam Metabolism," *Mol Pharmacol* 62: 162-172, 2002.
Torio et al., "Effect of CYP3A5*1/*3 Polymorphism on Blood Pressure in Renal Transplant Recipients," *Transplant Proc* 44:2596-2598, 2012.
Watlington et al., "Corticosterone 6b-hydroxylation correlates with blood pressure in spontaneously hypertensive rats," *Am J Physiol* 262: F927-F931, 1992.

* cited by examiner

*Primary Examiner* — Brian Whiteman
(74) *Attorney, Agent, or Firm* — Klarquist Sparkman, LLP

(57) ABSTRACT

Compositions and methods for treating hypertension in a subject are provided, including administering an antisense oligomer effective to reduce expression of cytochrome P450 3A5 (CYP3A5) enzyme. The antisense oligomer includes phosphorodiamidate morpholino oligonucleotide (PMO), phosphorothioate 2'-O-methyl oligoribonucleotides (PSO), locked nucleic acid nucleotide, locked nucleic acid analog nucleotide, or another modified oligonucleotide backbone or nuclease-resistant backbone. The antisense oligomer is administered transdermally, subcutaneously, or orally, and optionally with a pharmaceutically acceptable carrier. In one embodiment, the antisense oligomer is an oligomer that is antisense to mRNAs that encode CYP3A5, for instance targeted at the AUG start site of the mRNAs that encode CYP3A5 or at a G4 structure within CYP3A5.

15 Claims, 19 Drawing Sheets

Specification includes a Sequence Listing.

CYP3A4 Protein
1 – Scr Control
2 – CYP3A5- AUG PMO
3 – CYP3A4- AUG PMO

GAPDH Protein
4 – Scr Control
5 – CYP3A5- AUG PMO
6 – CYP3A4- AUG PMO

AUG Inhibitor of CYP3A5

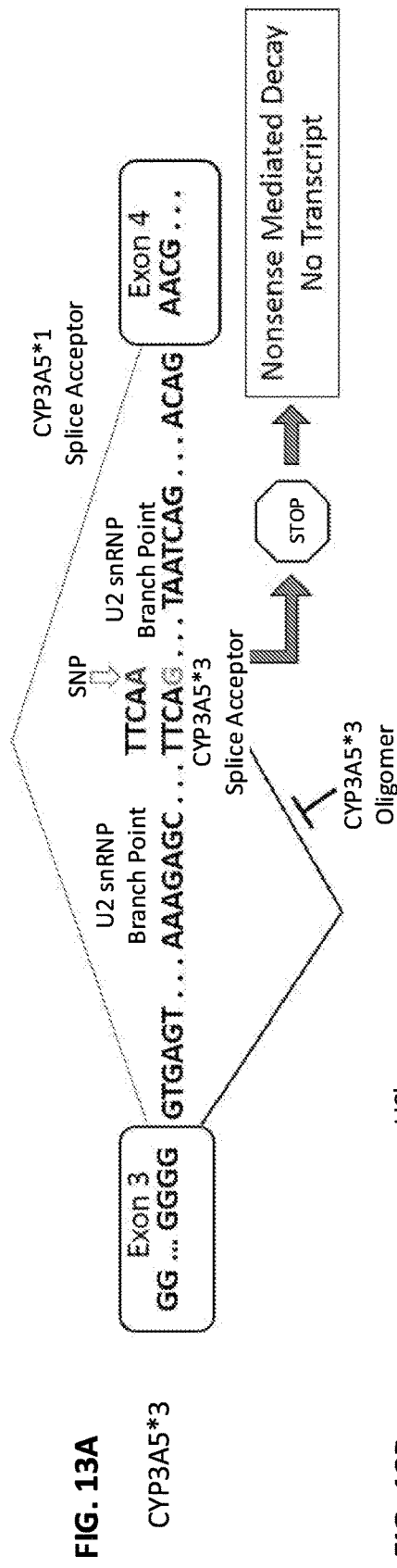
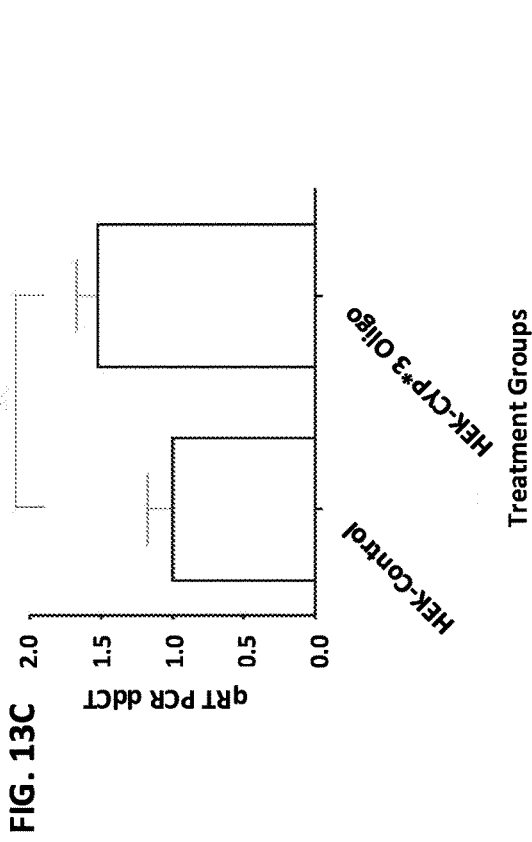
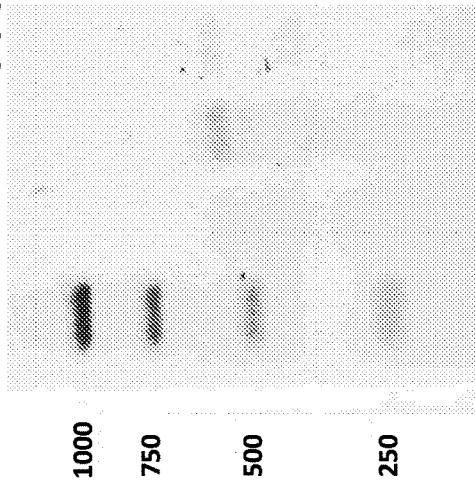
FIG. 13A
FIG. 13B
FIG. 13C

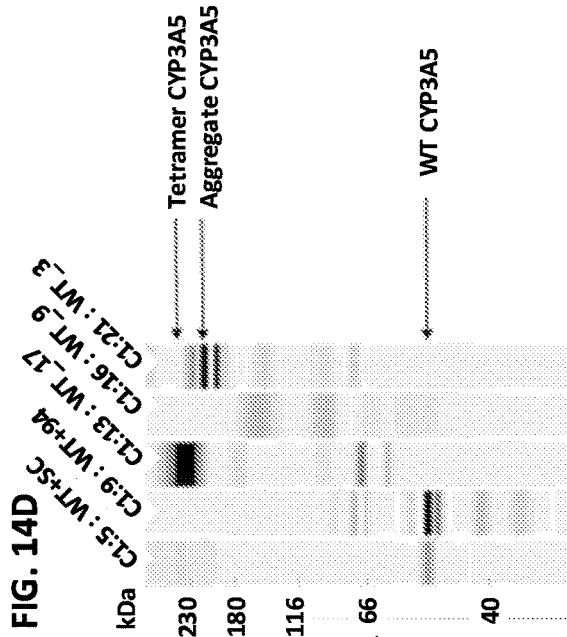
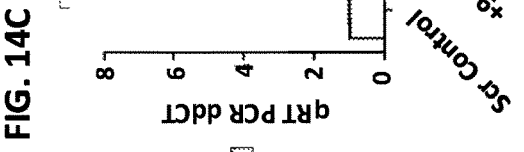
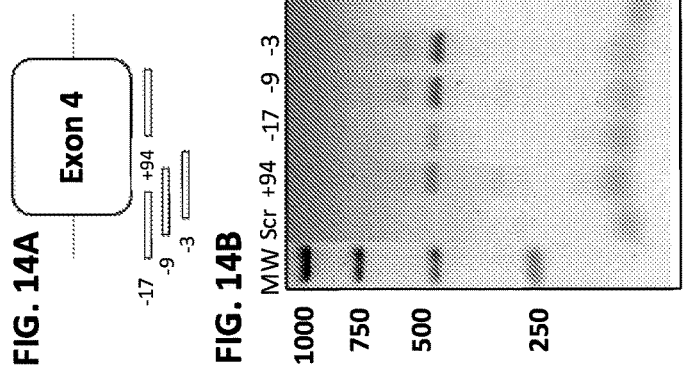

FIG. 16A
CYP3A5*3 Intron 3
5'...TAAAGAGCTCTTTGTCTTTCAG/TATCTCTTCCCTGTTGGACCACATTACCCTTCATCATGAAGCC
TTGGGTGGCTCCTGTGTGAGACTCTTGCTGTGTGTCACACCTAATGAACCTAGAAGGTTGCTGT
GTGTCGTACAACTAGGGTCGTATGGATTACACATAAATGATCAAAGTCTGGCTTCCTGGGTGGCTC
CAGCTGCAGAATCGGGCTAGTGAAGTTTAATCAGCTCCGTTGTCCCCACACAG/AACGTATGAAG...3'
                                                    Intron 3 / Exon 4
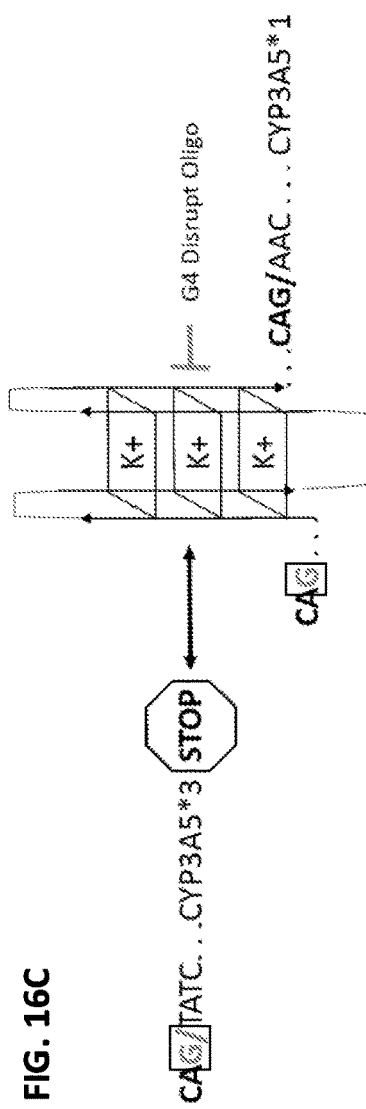
FIG. 16B
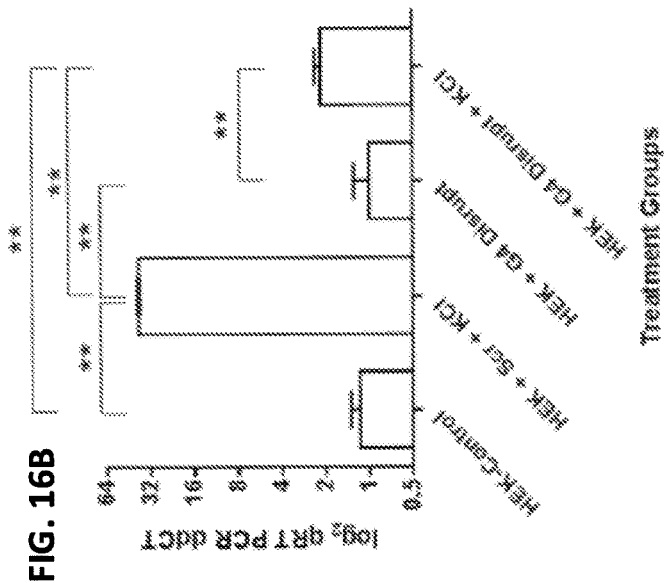
FIG. 16C

RENAL SELECTIVE INHIBITION OF CYTOCHROME P450 3A5

CROSS REFERENCE TO RELATED APPLICATION

This application is the U.S. National Stage of International Application No. PCT/US2016/050239, filed Sep. 2, 2016, published in English under PCT Article 21(2), which claims the benefit of U.S. Provisional Application No. 62/214,279, filed on Sep. 4, 2015, which is herein incorporated by reference in its entirety.

FIELD OF THE INVENTION

The present invention relates to methods and compositions for treating hypertension and, more particularly, to antisense oligomer compounds for renal selective inhibition of cytochrome P450 3A5 (CYP3A5) enzyme.

BACKGROUND

Over 1 billion people worldwide, and 31 percent of Americans, have hypertension or high blood pressure. Approximately 74.5 million adults over 20 years of age in the United States have high blood pressure. High blood pressure is characterized by a systolic blood pressure (SBP) of greater than 140 millimeters of mercury (mm Hg), a diastolic blood pressure (DBP) of greater than 90 mm Hg, or requiring antihypertensive medication. High blood pressure is the leading contributor to global mortality, with prevalence of 26.2 percent in the year 2000. Uncontrolled high blood pressure increases risk for stroke, diabetes, coronary heart disease, congestive heart failure, and chronic kidney disease. High blood pressure is associated with 4.9 to 5.1 years shorter life expectancy in women and men, respectively. Approximately three fourths of adults with cardiovascular disease (CVD) comorbidities experience poor control rates for systolic hypertension.

Long term trends indicate that approximately 55 percent of cases of high blood pressure have a heritable cause. In addition to heritability, risk factors for high blood pressure include increasing age, ethnicity, and behavior. Populations with darker skin color may have an unmet medical need for treatment of high blood pressure. Prevalence in African Americans in the United States is now 41.4 percent in men and 44.0 percent in women. The unmet medical need for new effective antihypertensive agents is paralleled by the $76.6 billion annual cost associated with high blood pressure.

Current therapy strategies for hypertension involve drugs to reduce cardiac output, decrease myocardial contractility, or lower peripheral resistance. Classes of current antihypertensive treatments include diuretics, adrenergic receptor antagonists, benzodiazepines, calcium channel blockers, renin inhibitors (aliskiren), angiotensin-converting enzyme (ACE) inhibitors, angiotensin II receptor antagonists, aldosterone receptor antagonists, vasodilators, adrenergic receptor agonists, endothelin receptor blockers (bosentan), and other emerging therapeutic approaches.

Diuretic therapies include loop diuretics (bumetanide, ethacrynic acid, furosemide, and torsemide), thiazide diuretics (epitizide, hydrochlorthiazide, chlorthiazide, and bendroflumethiazide), thiazide-like diuretics (indpamide, chlorthialidone, and metolazone), and potassium sparing (amiloride, triamterene, and spironolactone). Adrenergic receptor antagonists include beta-blockers (atenolol, metoprolol, nadolol, nebivolol, oxprenolol, propranolol, and timolol), alpha blockers (doxazosin, phentolamine, indoramin, phenoxybenzamine, prazocin, terazosin, and tolazoline), mixed alpha/beta blockers (bucindolol, carbedilol, and labetalol), and indirect or central (guanethidine, reserpine, and mecamylamine, which is an anti-nicotinic). Calcium channel blockers include dihydropyridines (amlodipine, cilnidipine, felodipine, isradipine, lercanidipine, levamlodipine, nicardipine, nimodipine, and nitrendipine). ACE inhibitors include drugs such as captopril, enalapril, fosinopril, lisinopril, perindopril, quinapril, ramipril, trandolapril, and benazepril. Angiotensin II receptor antagonists include drugs such as candesartan, eprosartan, irdesartan, losartan, olmesartan, telmisartan, and valsartan. Aldosterone receptor antagonists include drugs such as eplerenone and spironolactone, which treats heart failure. Vasodilators include drugs such as minoxedil, sodium nitroprusside, and hydrazaline. Adrenergic receptor agonists of the subclass $\alpha_2$, include clonidine, guanabenz, guanfacine, methyldopa, and moxonidine. Other emerging therapeutic approaches include blood pressure vaccine CYT006-AngQb and renal denervation using a radiofrequency ablation catheter.

Current approaches using substrate inhibitors are unable to separate inhibition of cytochrome P450, family 3, subfamily A, polypeptide 5 (CYP3A5) and cytochrome P450, family 3, subfamily A, polypeptide 4 (CYP3A4). Substrate inhibitors for the CYP3A family of enzymes typically have a molecular weight of approximately 150 to 350 grams per mole, and sit in the active site of a receptor to block the enzymes from binding to the receptor. Substrate inhibitors are broad, in that the substrate inhibitors for CYP3A5 also block or inhibit CYP3A4 along with other CYP3A enzymes and potentially other cytochrome P450s in the body. The lack of specificity of substrate inhibitors can result in undesirable side effects, such as inhibiting or decreasing the metabolic activity of other cytochrome P450s. Substrate inhibitors can further cause reactive metabolite formation, for example, when molecular oxygen ($O_2$) is broken from $O_2$ into reactive oxygen during CYP3A5 metabolism. Reactive metabolite byproducts of CYP3A5 metabolism create intermediate superoxides that can become hydroxyl radicals, which can accumulate in the kidney and are damaging to cells.

Some patients are refractory to the current standard of care in managing hypertension and continue to suffer from uncontrolled hypertension while using current treatments. Emerging populations of individuals are not able to control blood pressure with the wide variety of current medications currently available to treat hypertension. Additionally, renal transplant patients taking antirejection immune suppression drugs such as cyclosporin A or tacrolimus are at risk of kidney transplant rejection due to enhanced renal clearance from CYP3A5 metabolism.

Attempts to unravel the strong genetic linkage to hypertension have not led to genetic profiles for prediction or development of new therapeutics to treat hypertension. Initial genome wide associative studies (GWAS) to identify genes contributing to human hypertension failed to identify any single-nucleotide polymorphisms (SNPs) corresponding to hypertension. Subsequently, larger GWAS identified genes associated with hypertension in African Americans and variants contributing to population SBP, but the studies fail to reproducibly identify the same genes, or genes with impact greater than 1 to 2 mm Hg in blood pressure, or provide mechanistic insights into the genetic basis of hypertension. The GWAS do not lead to useful genetic profiles for predicting hypertension. The apparent contradiction between heritability of hypertension and failure of GWAS to find significant genetic linkage can be explained by the emerging complexity in ribonucleic acid (RNA) expression.

SUMMARY OF THE INVENTION

A need exists for a treatment for hypertension that avoids the problems with a substrate inhibitor, has gene-specific capability, and is effective at a low dose. Accordingly, in one embodiment, the present invention is a method of treating hypertension in a subject comprising administering an antisense oligomer effective to reduce expression of cytochrome CYP3A5 enzyme.

In another embodiment, the present invention is a composition comprising an antisense oligomer including any one of SEQ ID NOs: 1-7. In one embodiment, the antisense oligomer is an oligomer that is antisense to mRNAs that encode CYP3A5, for instance targeted at the AUG start site of the mRNAs that encode CYP3A5 or at a G4 structure within CYP3A5. The antisense oligomer in various embodiments reduces production of CYP3A5, which reduces salt retention and salt-induced hypertension in the subject.

Thus, there is contemplated in one embodiment a method of treating hypertension in a subject, comprising administering (for instance, transdermally) a non-naturally occurring antisense oligomer effective to reduce or modify expression of cytochrome CYP3A5 enzyme. By way of examples of this embodiment, the antisense oligomer used in the method may include the sequence of SEQ ID NO: 1, SEQ ID NO: 2, SEQ ID NO: 3, SEQ ID NO: 4, SEQ ID NO: 5, SEQ ID NO: 6, or SEQ ID NO: 7. In additional examples, the antisense oligomer overlaps the sequence of any one of SEQ ID NO: 1, SEQ ID NO: 2, SEQ ID NO: 3, SEQ ID NO: 4, SEQ ID NO: 5, SEQ ID NO: 6, or SEQ ID NO: 7 with a free energy between −25 and −35 kilocalories per mole (kcal/mol). In any of these examples, the antisense oligomer may comprise a phosphorodiamidate morpholino oligonucleotide (PMO), a phosphorothioate 2'-O-methyl oligoribonucleotide (PSO), a locked nucleic acid nucleotide, or locked nucleic acid analog nucleotide, or another modified oligonucleotide backbone or nuclease-resistant backbone, or any combination thereof. Optionally, the antisense oligomer is administered transdermally, subcutaneously, or orally, and optionally with a pharmaceutically acceptable carrier.

Also provided are composition embodiments, which compositions comprise in one example an antisense oligomer including the sequence of SEQ ID NO: 1 or overlapping the sequence of SEQ ID NO: 1 with a free energy between −25 and −35 kilocalories per mole (kcal/mol); or in another example an antisense oligomer including the sequence of SEQ ID NO: 4 or overlapping the sequence of SEQ ID NO: 4 with a free energy between −25 and −35 kilocalories per mole (kcal/mol); or in another example an antisense oligomer including the sequence of SEQ ID NO: 5 or overlapping the sequence of SEQ ID NO: 5 with a free energy between −25 and −35 kilocalories per mole (kcal/mol); or in another example an antisense oligomer including the sequence of SEQ ID NO: 6 or overlapping the sequence of SEQ ID NO: 6 with a free energy between −25 and −35 kilocalories per mole (kcal/mol); or in yet another example an antisense oligomer including the sequence of SEQ ID NO: 7 or overlapping the sequence of SEQ ID NO: 7 with a free energy between −25 and −35 kilocalories per mole (kcal/mol). Optionally, such compositions may further include (comprise) a pharmaceutically acceptable carrier.

BRIEF DESCRIPTION OF THE DRAWINGS

FIG. 12B shows Western blot using (left panel) antibody to CYP3A5 and (right panel) internal control GAPDH.

FIG. 13A illustrates the sequence of the Exon 3/Exon 4 boundary in FHEK293 cells CYP3A5*3 (SEQ ID NO: 3). FIG. 13B is a photo of the results of endpoint RT-PCR, and FIG. 13 C is qRT-PCR which reveals a significant shift in expression from *3 to *1; $p=0.0037$.

FIG. 14A-14D illustrates the construction and analysis of oligonucleotides for influencing expression of CYP3A5. FIG. 14A illustrates the locations of phosphorodiamidate morpholino oligomers (PMO) that were designed to bind to the splice acceptor region of exon 4 (−17, −9, and −3) [SEQ ID NOs: 5, 6, 7, and 8], as well as the splice donor region of exon 4 (+94) which were compared to scrambled sequence PMO. FIG. 14B is a photo of the results of endpoint PCR of CYP3A5 mRNA from HEK293 cells, after treatment with each of the PMOs. HEK293 cells do not express a stable CYP3A5*3 transcript when exposed to a scrambled sequence oligomer (Scr), but PMO binding to exon 4 induce exon inclusion and the expression of a stable CYP3A5 transcript. The PMO targeting the splice acceptor region at −3 and −9 are more effective in exon 4 inclusion. FIG. 14C is a graph of quantitative PCR (qRT PCR) evaluation of HEK293 cells oligomers targeting exon 4 (−17, −9, and −3) [SEQ ID NOs: 5, 6, 7, and 8] as well as the splice donor region of exon 4 (+94) which were compared to scrambled sequence PMO. FIG. 14D is a scan of a western blot from HEK293 cells incubated with oligomers targeting exon 4 (−17, −9, and −3) [SEQ ID NOs: 5, 6, 7, and 8] as well as the splice donor region of exon 4 (+94) which were compared to scrambled sequence PMO.

FIG. 16A is the TA portion of the sequence from CYP3A5*3 intron 3 (positions 1647 to 1916 of SEQ ID NO: 12) with the SNP shown by arrow and the putative elements of the G4 structure in bold. FIG. 16B is a graph showing qRT-PCR quantification of CYP3A5 in the presence of G4 disruptor SEQ ID NO: 2 in the indicated salt conditions; ** indicates p<0.01. FIG. 16C illustrates the G4 structure of the CYP3A5*3 splice acceptor in intron 3 (indicated by the boxed G/) which leads to NMD (indicated by the STOP), but the G4 structure induced by KCl shifts the splice acceptor to the CAG/site at exon 4. Incubation of the cells with the G4 disrupt oligomer SEQ ID NO: 2 prevents the formation of the G4 structure indicated by the red symbol and the splice acceptor is shifted back to the intron 3 site indicated with the boxed G/.

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file created on Feb. 9, 2018, 23.8 KB, which is incorporated by reference herein In the accompanying Sequence Listing:

SEQ ID NO: 1 is the nucleotide sequence of the CYP3A5 AUG Suppressor (a.k.a., hCYP3A5_AUG_Suppresor) oligomer, which targets the Exon 1—Start Site.

SEQ ID NO: 2 is the nucleotide sequence of the hCYP3A5_*1 oligomer, which targets Intron 3—6986A.

SEQ ID NO: 3 is the nucleotide sequence of the CYP3A5*3 (a.k.a., hCYP3A5_*3) oligomer, which targets Intron 3—6986A>G.

SEQ ID NO: 4 is the nucleotide sequence of the CYP3A5 G4 disrupter (a.k.a., hCYP3A5_G4_Disruptor) oligomer, which targets Intron 3—7162G.

SEQ ID NO: 5 is the nucleotide sequence of the CYP3A5dex4(−3,19) (a.k.a., hCYP3A5_dex4_(−3,19)) oligomer, which targets Exon 4—SA.

SEQ ID NO: 6 is the nucleotide sequence of the CYP3A5dex4(−9,16) (a.k.a., hCYP3A5_dex4_(−9,16)) oligomer, which targets Exon 4—SA.

SEQ ID NO: 7 is the nucleotide sequence of the CYP3A5dex4(−17,5) (a.k.a., hCYP3A5_dex4_(−17,5)) oligomer, which targets Exon 4—SA.

SEQ ID NO: 8 is the nucleotide sequence of the CYP3A5dex4(+94,118) (a.k.a., hCYP3A5_dex4_(+94, 118)) oligomer, which targets Exon 4—SD.

SEQ ID NO: 9 is the nucleotide sequence of the Scramble Control oligomer, which has no target sequence within CYP3A5.

SEQ ID NOs: 10 and 11 are forward and reverse (respectively) oligomers for PCR amplification CYP3A5 mRNA.

SEQ ID NO: 12 is the nucleotide sequence of Human CYP3A5.

SEQ ID NO: 13 is the nucleotide sequence of Chimpanzee CYP3A5.

SEQ ID NO: 14 is the nucleotide sequence of Marmoset CYP3A5.

SEQ ID NO: 15 is the nucleotide sequence of Rhesus monkey CYP3A5.

SEQ ID NO: 16 is the nucleotide sequence of Cynomolgus monkey CYP3A5.

SEQ ID NO: 17 is the nucleotide sequence of Rat CYP3A9.

SEQ ID NO: 18 is the nucleotide sequence of Mouse CYP3A13.

SEQ ID NO: 19 is the nucleotide sequence of Zebrafish CYP3C1.

DETAILED DESCRIPTION OF THE DRAWINGS

The present invention is described in one or more embodiments in the following description with reference to the figures, in which like numerals represent the same or similar elements. While the invention is described in terms of the best mode for achieving the invention's objectives, it will be appreciated by those skilled in the art that it is intended to cover alternatives, modifications, and equivalents as may be included within the spirit and scope of the invention as defined by the appended claims and their equivalents as supported by the following disclosure and drawings.

Figure 1:
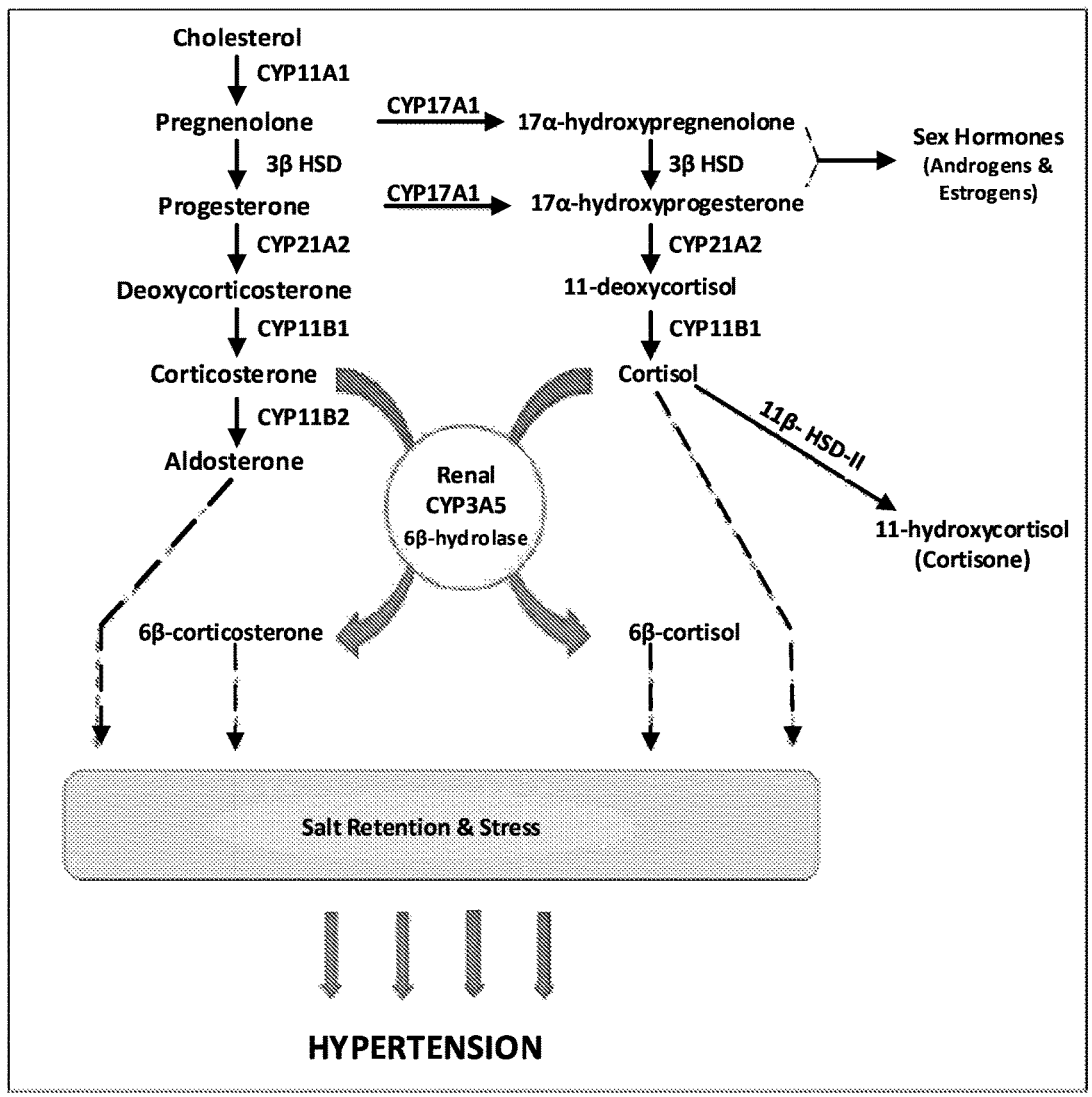
FIG. 1 illustrates the mechanism of action of CYP3A5 enzyme.

FIG. 1 shows the mechanism of action of CYP3A5 enzyme and the relationship of CYP3A5 to hypertension. Glucocorticoids, including cortisol and corticosterone, are associated with the control of blood pressure. Glucocorticoids, including cortisol and corticosterone, bind to the glucocorticoid receptor (GCR) in a target cell. Glucocorticoids also enhance the transcription of CYP3A5. CYP3A5 is the primary CYP3A isoform expressed in the human kidney and is associated with hypertension. Cytochrome P450 enzymes, including CYP3A5, are heme-containing proteins and use a heme iron in the active site, rather than a lock-and-key type mechanism. CYP3A5 catalyzes the 6β hydroxylation of glucocorticoids, such as cortisol and corticosterone. The oxidation-reduction reaction or redox reaction of CYP3A5 uses the heme iron to break the molecular oxygen and uses the reactive oxygen to modify the substrate. Cortisol and corticosterone are hydroxylated at the 6 position to make 6-β-cortisol and 6-β-corticosterone, which are 6-β-hydroxylase (6-β-OH) products. The 6-β-OH products are inactive ligands for the GCR, but activate the mineralocorticoid receptor (MR).

The renal localization of CYP3A5 in the proximal tubule and collecting duct of the kidney can convert glucocorticoids such as corticosterone to metabolic products such as 6-β-corticosterone, thereby shifting endogenous signaling from the GCR to paracrine signaling through the MR. The action of the MR leads to salt retention, which in turn can lead to hypertension. In addition, CYP3A5 metabolism inactivates several immune suppressing drugs including cyclosporine and tacrolimus, so that elevated expression of CYP3A5 may lead to kidney transplant rejection.

Alterations in the level of CYP3A5 expression disturbs the homeostasis of endogenous metabolites such as glucocorticoids, steroid hormones, bile acids, and retinoids. Reducing expression of CYP3A5 in the kidney re-directs metabolism of cortisol and corticosterone away from 6-β-OH products, including 6-β-cortisol and 6-β-corticosterone, that may interfere with the renin-angiotensin system. The present disclosure provides antisense oligomer compositions and methods for inhibiting expression of CYP3A5 enzyme in the kidney for the treatment of hypertension and prevention of organ transplant rejection.

Figure 2:
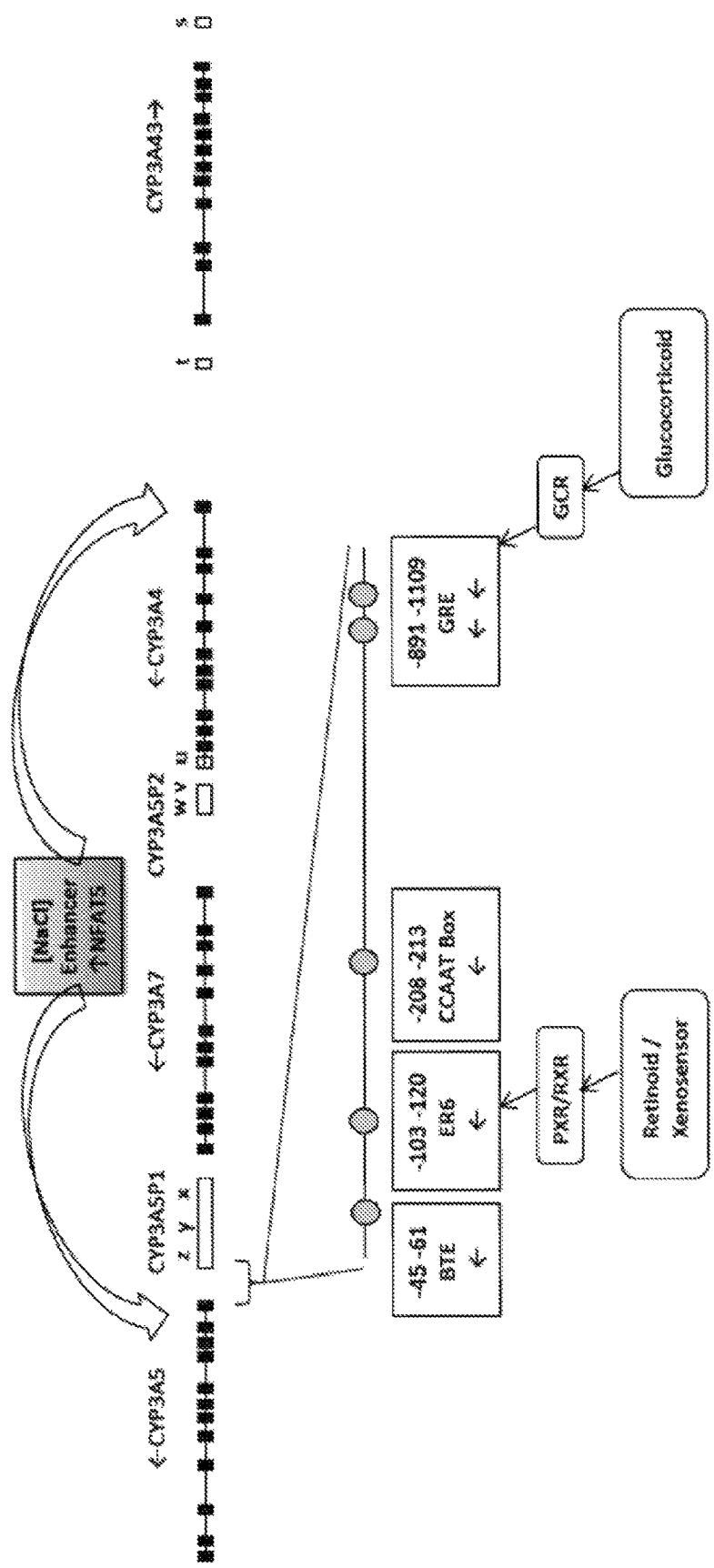
FIG. 2 illustrates the CYP3A cluster and regulation of CYP3A5 expression.

FIG. 2 shows the CYP3A cluster and regulation of CYP3A5. The human cytochromes P450 are a group of heme-thiolate monooxygenases, often associated with the endoplasmic reticulum of the cell, that oxidize a variety of structurally unrelated substrates including steroids, fatty acids, and xenobiotics including drugs such as tacrolimus. The cytochrome P450 3A (CYP3A) family of enzymes is located in a cluster of isoenzymes encoded in about 200 kilo-bases (kb) on chromosome 7. More specifically, CYP3A5 is located on chromosome 7q22.1 in part of a cluster of 13-exon containing CYP3A genes: CYP3A5, CYP3A7, CYP3A4, and CYP3A43 as well as two pseudogenes, CYP3A5P1 comprising three exons and CYP3A5P2 comprising two exons, and fragments that are single exon appearances spaced within the cluster.

CYP3A5 and CYP3A4 have structural similarities, and 26 amino acid differences out of approximately 502 amino acids, resulting in similar substrate specificities for CYP3A5 and CYP3A4. Even with the similarity in enzymatic activity and structure, the expression profile of CYP3A5 differs from the expression profile of CYP3A4. CYP3A4 is expressed in the liver and small intestine, and metabolizes a substantial number of drug types. CYP3A5, unlike CYP3A4, is expressed in steroidogenic organs including the prostate, adrenal, and kidney, as well as the lung and liver. CYP3A5 encodes several structurally similar protein variants involved in synthesis of cholesterol, steroids, and other lipids.

The promoter for CYP3A5 is detailed in FIG. 2. The basal level enhancer (BTE) is shown −45 to −61 base pairs (bp) upstream from the translation start site and represents the region of the gene that maintains a steady state level. The promoter for CYP3A5 includes ER6 located −103 to −120 bp upstream. ER6 is sensitive to regulation by the pregnane X receptor (PXR) or the retinoid X receptor (RXR). The CCAAT box, the transcription recognition site for transcription from the RNA polymerase, is located −208 to −213 bp upstream from the translation start site. The glucocorticoid response element (GRE) is located −891 to −1109 bp upstream and is not continuous, but instead GRE includes two half-sites, and is less sensitive to glucocorticoid than CYP3A4. Therefore, the driver of the CYP3A5 is almost exclusively BTE.

As discussed above, alterations in the level of CYP3A5 expression disturbs the homeostasis of endogenous metabolites such as glucocorticoids as well as steroid hormones, bile acids, and retinoids. The kidney CYP3A5 product homeostasis is not as easily disrupted as CYP3A4 homeostasis due to a low expression of PXR nuclear hormone receptor and due to a 57 base pair deletion in the CYP3A5 promoter, relative to the CYP3A4 promoter, containing a repressive transcriptional cis-element. The CYP3A5 promoter is responsive to glucocorticoids due to the two GRE half-sites, TGTTCT, which require greater amounts of GCR signal to activate transcription. CYP3A5 transcription is enhanced by glucocorticoids like corticosterone. CYP3A5 transforms corticosterone to 6-β-corticosterone, which is an inactive ligand for the GCR but activates the MR and salt retention.

CYP3A7, located about 10 kb away from CYP3A5, contains a salt-sensitive enhancer that upregulates the expression of CYP3A5. Salt binds to a tonicity-responsive enhancer (TonE) located in intron 2 of CYP3A7. TonE acts as an enhancer for neighboring CYP3A4 and CYP3A5 through a binding protein, NFAT5, leading to salt induced CYP3A5 expression, increased production of 6-β-corticosterone, and an amplification of salt responsiveness resulting in hypertension and subsequent CVD-related pathogenesis. Thus, through the CYP3A7 enhancer, salt drives the upregulation of CYP3A5 which causes salt retention, creating an amplifying loop.

Figure 3:
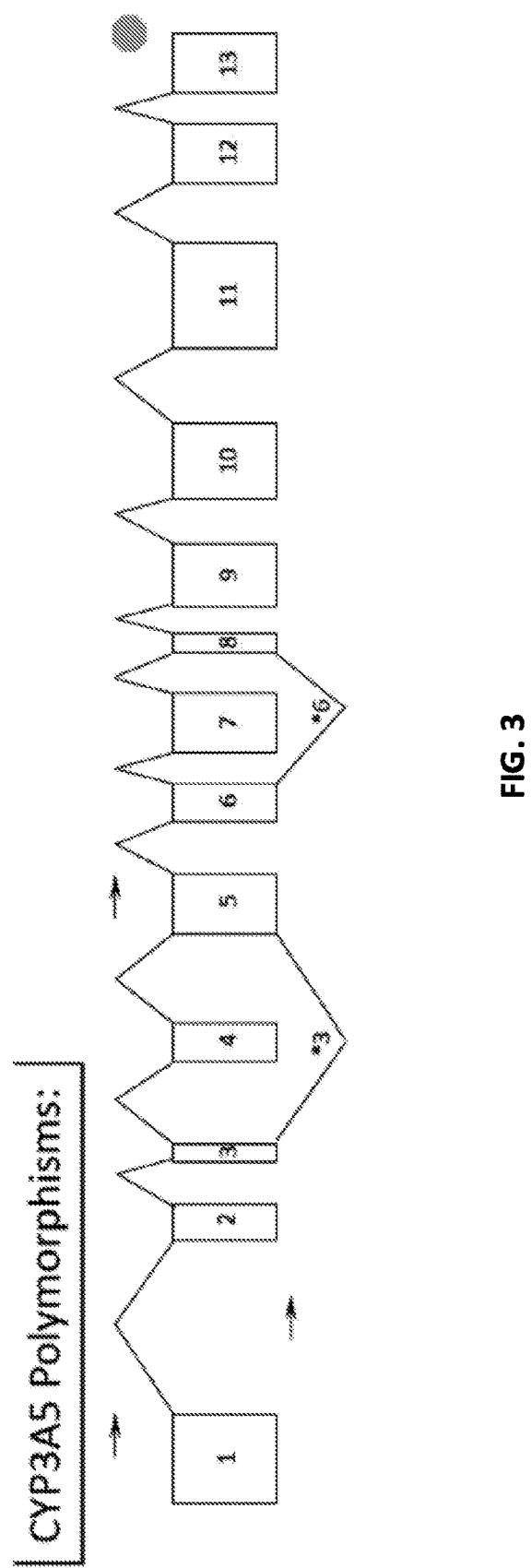
FIG. 3 illustrates alternate exon gene structure for CYP3A5, including polymorphisms.

FIG. 3 shows alternate exon gene structures for CYP3A5. CYP3A5 is polymorphic with over 11 different alleles. The polymorphism CYP3A5*1 is a functional allele containing 13 exons, with no exons skipped, and is found primarily in African Americans. Polymorphism CYP3A5*3 is an allele having a 6986A>G mutation in intron 3 that leads to production of an aberrant messenger RNA (mRNA) and a 102 amino acid truncated protein, and deletes exon 4. CYP3A5*3 is found primarily in Caucasians. A 14,690G>A mutation induces a splice variant deleting exon 7 of CYP3A5*6, which encodes a nonfunctional protein found in 13% of African Americans and 0% in Caucasians. A 23,132insT mutation creates a premature stop codon in CYP3A5*7 mRNA.

In a group of 25 African American subjects, elevated SBP was observed in those with homozygous CYP3A5*1/*1 genotype compared to heterozygous CYP3A5*1/*3 and homozygous CYP3A5*3/*3 genotypes. Two studies with 683 subjects were genotyped as CYP3A5*1/*1, CYP3A5*1/*3, and CYP3A5*3/*3 in which virtually all of the CYP3A5*1/*1 were African American subjects and a total of 38 percent of Caucasians and 58 percent of the African American subjects were hypertensive establishing a linkage between CYP3A5*1/*1 and hypertension. Of those African American hypertensive subjects, 63.6% failed to achieve SBP control in the CYP3A5*1/*1 genotype while all CYP3A5*3/*3 were able to achieve SBP control. In another study, no significant differences in SBP or DBP frequencies based on CYP3A5*3 or CYP3A5*6 allele status were observed but SBP frequency was higher in CYP3A5*1 alleles (p=0.061). The precise relationship between CYP3A5 polymorphisms and hypertension is unresolved. In one study, CYP3A5*1 was associated with elevated SBP. In another study, CYP3A5*3/*3 was associated with higher SBP. In yet another study, CYP3A5*1 allele was associated with SBP in African Americans but not Caucasians. Another study showed the CYP3A5*1 allele was associated with lower SBP, although the study did not consider CYP3A5*1/*1 homozygous alleles.

Approximately 50 percent of human genetic diseases arise due to mutations that affect splicing. The presence of the polymorphism CYP3A5*1, either as heterozygous CYP3A5*1/*3 and homozygous CYP3A5*1/*1, results in the individual expressing the enzyme that causes salt retention. Typically, individuals with homozygous CYP3A5*3/*3 do not have the enzyme that causes salt retention. However, the allele linkage to hypertension is further complicated by the fact that CYP3A5*3/*3 individuals can express wild type CYP3A5. The sequence context of the exon junctional complex (EJC) may weakly or strongly define an exon, and mutations in the 5'-donor or 3'-acceptor region tend to diminish but not necessarily extinguish spliceosome recognition. Additional regulation of splicing involves cis-elements referred to as intronic splicing silencers (ISS), intronic splicing enhancers (ISE), exonic splicing silencers (ESS), exonic splicing enhancers (ESE), and trans-acting proteins which are generally members of the serine rich (SR) protein family.

Figure 4:
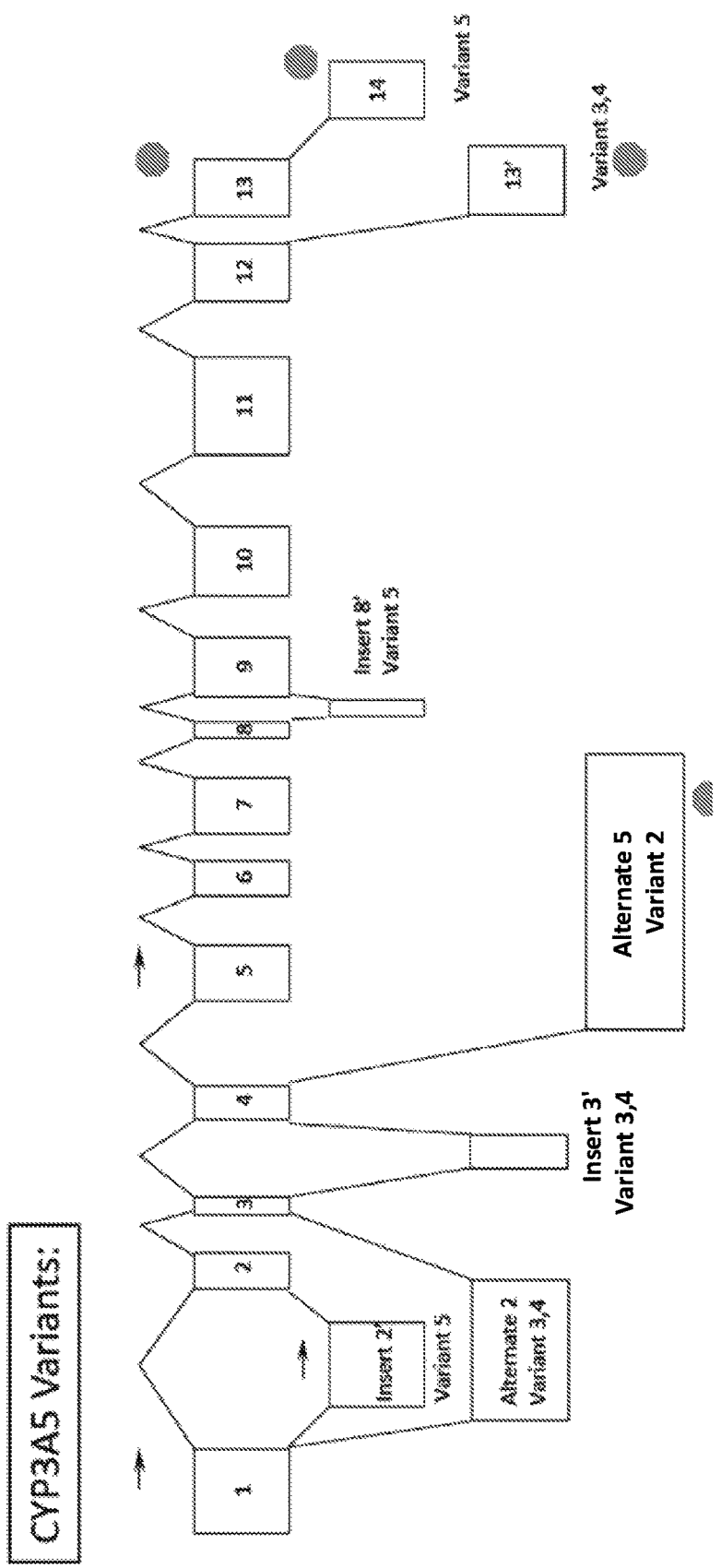
FIG. 4 illustrates additional alternate exon gene structure for CYP3A5, including variants.

FIG. 4 shows variants for CYP3A5, including inserted exons and alternative exons. The arrows in FIG. 4 represent translation start sites. A translation start site at exon 1 is the most active site. The translation start site at exon 2 possibly produces an active protein. The translation start site at exon 5 is expected to not produce an enzyme that would fit into the cell membrane, thereby separating the enzyme from its reductase partner, and resulting in a non-metabolically active protein. A translation inhibitor does not always block production of the protein, because translation can begin at a translation start site downstream of the inhibitor.

RNA sequencing (RNAseq) data for CYP3A5 reveals a variety of variants including alternate exon use, alternate translation start sites, and alternate termination sites. A summary of the observations include: 13 exons reported in NM_000777.3; exon 2 is enlarged and a new exon is included in NR_033808.1; the translation start site is delayed and the gene is truncated to 11 exons in XM_006715859.1; and the gene is truncated at 5 exons with a delayed translational start site in NM_001190848.1. The invention uses techniques of exon skipping, alternate translation start site shifting, and nonsense-mediated decay (NMD) induction to interrogate CYP3A5-specific mechanisms controlling 6-β-hydroxylase activity, aldosterone levels, and regulation of salt homeostasis.

An NMD approach involves the proof-reading function at the RNA level, which degrades transcripts that do not comply with the reading frame. For example, where exon 4 is skipped in the CYP3A5*3 polymorphism, the gene is put out of reading frame. Once the gene is out of frame and the mRNA encounters a premature termination codon before reaching the EJC, degradation is triggered for that transcript. Therefore, CYP3A5*3 are degraded by NMD. Alternate translation start sites and alternate exon use patterns of gene expression may represent endogenous regulatory mechanisms to limit expression of CYP3A5. Hence, most of the alterations in expression lead to reduced expression of the enzyme in the kidney, CYP3A5, which is capable of producing 6-β-corticosterone. The antisense therapy is expected to achieve reduction in CYP3A5 in individuals that are not able to limit expression of CYP3A5.

Figure 5A:
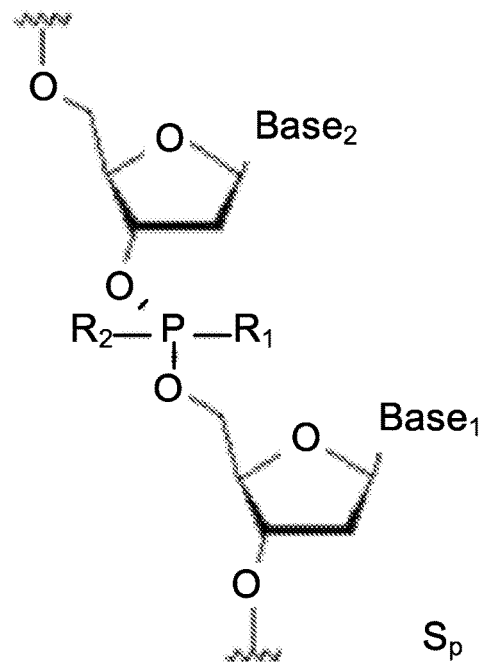
FIGS. 5A-5C illustrate synthetic deoxyribonucleic acid (DNA) and RNA analogs.
Figure 5B:
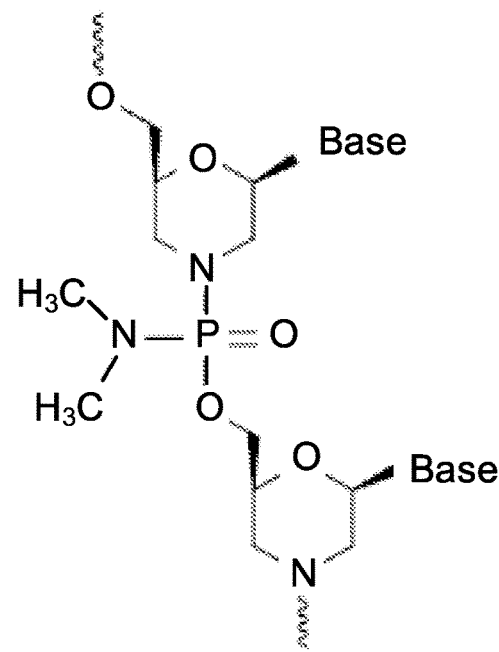
Figure 5C:
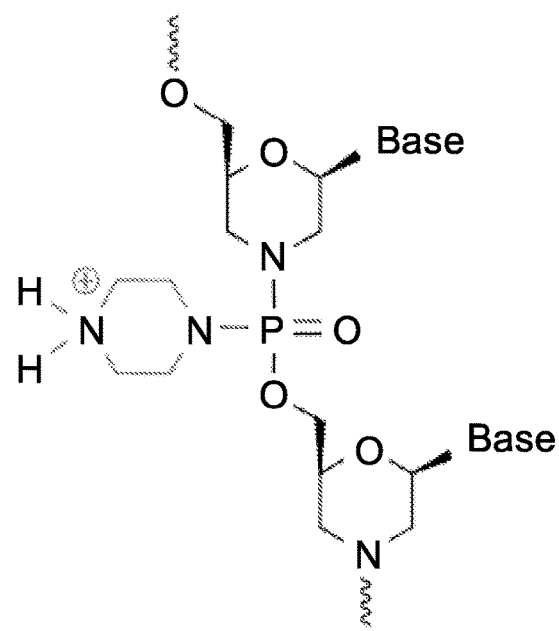
Figure 6A:
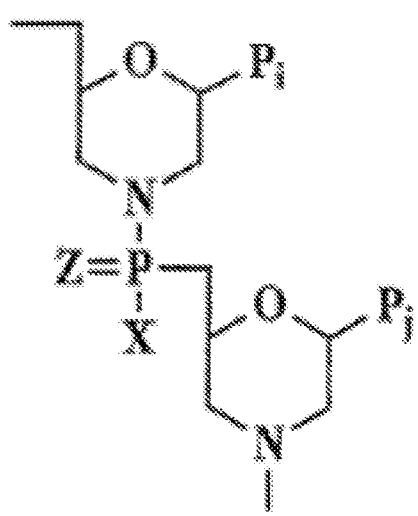
FIGS. 6A-6D illustrate examples of subunits and linkages of morpholino oligomers.
Figure 6B:
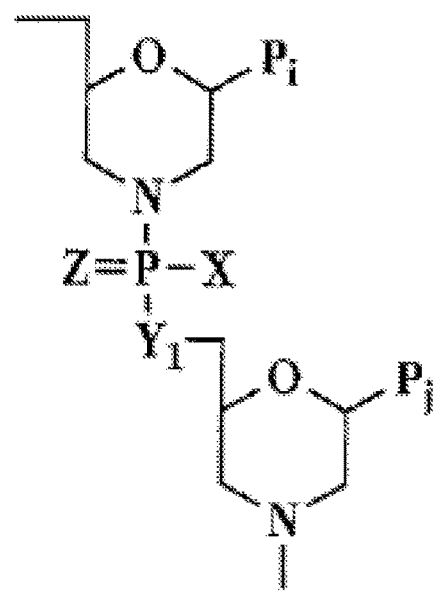
Figure 6C:
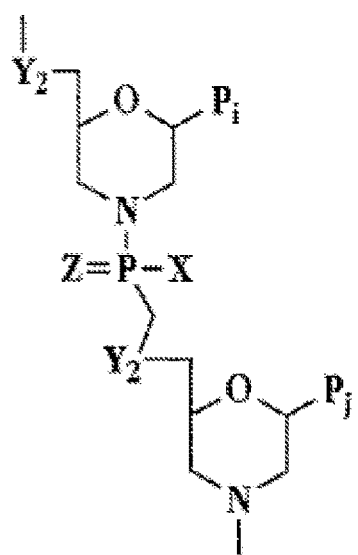
Figure 6D:
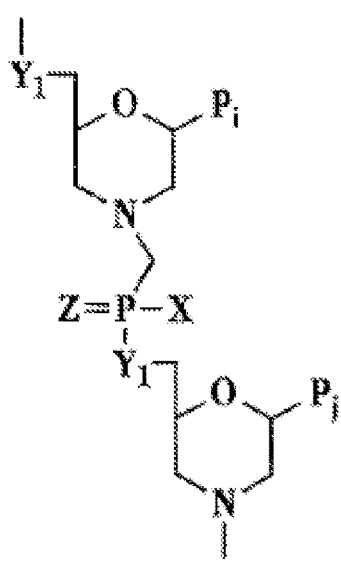

FIGS. 5A-5C show compounds useful in antisense methods including synthetic DNA or RNA analogs. The present invention comprises an antisense approach to inhibition of CYP3A5 expression. An antisense molecule is a synthetic nucleic acid polymer. Antisense oligomers effect changes in gene expression and protein production by the complementary hybridization of oligonucleotides to DNA or RNA, such that the normal functions of intracellular nucleic acids are disrupted. Antisense oligomers, i.e., oligonucleotides or oligonucleotide analogs, include a sequence of nucleotide bases that bind to a target sequence in RNA by Watson-Crick base pairing. The antisense oligomer may have exact sequence complementarity to the target sequence or near complementarity. In one embodiment, the antisense oligomer containing the complimentary sequence binds to mRNA or to precursor mRNA (pre-mRNA) in the cell nucleus to block translation of mRNA containing the target sequence.

In one embodiment, a 23 residue oligonucleotide (23-mer) sequence that blocks translation of mRNA into CYP3A5 includes SEQ ID NO: 1, shown in Table 1. In another embodiment, the antisense oligomer includes a sequence that overlaps SEQ ID NO: 1 and can be any sequence that overlaps SEQ ID NO: 1 with a free energy (dG) between −25 and −35 kilocalories per mole (kcal/mol). In some embodiments, the antisense oligomer includes up to about 20 flanking nucleotides upstream and/or downstream of the sequence of SEQ ID NO: 1. In additional embodiments, the antisense oligomer overlaps any one of SEQ ID NOs: 2-7 and can be any sequence that overlaps with one of SEQ ID NOs: 2-7 with a free energy (dG) between −25 and −35 kilocalories per mole (kcal/mol). Oligonucleotides of different length are specifically contemplated, such as oligomers (e.g., antisense oligomers) of about 20 to about 100 nucleotides in length; for instance, 20-90, 20-80, 20-70, 20-60, 20-50, 20-40, or 20-30 nucleotides in length.

TABLE 1

| ID NO | Sequence 5'-3' | Name | Target |
|---|---|---|---|
| 1 | TTTCCCATGAGGTCCATCGCCAC | hCYP3A5_AUG_Suppresor | Exon 1-Start Site |
| 2 | CAGGGAAGAGATATTGAAAGAC | hCYP3A5_*1 | Intron 3-6986A |
| 3 | CAGGGAAGAGATACTGAAAGAC | hCYP3A5_*3 | Intron 3-6986A > G |
| 4 | CCGATTCTGCAGCTGGAGCCACAC | hCYP3A5_G4_Disruptor | Intron 3-7162G |
| 5 | GAGTTGACCTTCATACGTTTCTG | hCYP3A5_dex4_(-3, 19) | Exon 4-SA |
| 6 | TTGACCTTCATACGTTCTGTGTGGG | hCYP3A5_dex4_(-9, 16) | Exon 4-SA |
| 7 | ACGTTCTGTGTGGGACAACGG | hCYP3A5_dex4_(-17, 5) | Exon 4-SA |
| 8 | CAAAAAATGGATGCTTACCCTTCGA | hCYP3A5_dex4_(+94, 118) | Exon 4-SD |
| 9 | ACTCCATCGTTCAGCTCTGA | Sequence scrambled control | N/A |

The term "oligonucleotide analog" refers to an oligonucleotide having a modified backbone structure, such as a backbone other than the standard phosphodiester linkage found in natural oligo- and polynucleotides, and optionally, modified sugar moieties, such as morpholino moieties rather than ribose or deoxyribose moieties. The oligonucleotide analog supports bases capable of hydrogen bonding by Watson-Crick base pairing to standard polynucleotide bases. The oligonucleotide analog backbone presents the bases in a manner to permit such hydrogen bonding in a sequence-specific fashion between the oligonucleotide analog molecule and bases in a standard polynucleotide, such as single-stranded RNA or single-stranded DNA. In one embodiment, the oligonucleotide analog has a substantially uncharged, phosphorus containing backbone. Non-ionic oligonucleotide analogs, i.e., oligomers having uncharged backbones, include phosphotriester- and methylphosphonate-linked DNA, carbamate-linked nucleosides, phosphoroamidate-linked DNA, and peptide nucleic acids (PNA).

In one embodiment, the antisense oligomer includes a nuclease-resistant oligomer, which has a backbone not susceptible to nuclease cleavage. Nuclease-resistant antisense oligomers are oligonucleotide analogs and may have charged (polyanionic or polycationic) backbones or uncharged backbones. FIG. 5A shows a structure for polyanionic synthetic genetic material, which includes a negatively charged backbone. In one embodiment, $R_1$ and $R_2$ are selected from oxygen, sulfur, boron, and a borane moiety such as $BH_3—$. Polyanionic includes phosphorothioate, boranophosphates, phosphorodithioates, and phosphate-amine DNA (pnDNA). FIG. 5B shows an example of a structure for neutral synthetic genetic material. Neutral synthetic genetic material includes triesters, methylphosphontes, phosphoramidates, PNA, and phosphorodiamidate morpholinos (PMO). FIG. 5C shows an example of a structure for polycationic synthetic genetic material, which includes arginine-PMO (arg-PMO) and PMOplus.

In one embodiment, the oligomer structure employs morpholino-based subunits bearing base-pairing moieties, joined by uncharged linkages. The morpholino oligomer or morpholino oligonucleotide is a polymeric molecule having a backbone which supports bases capable of hydrogen bonding to typical polynucleotides. The polymer lacks the ribose backbone linked by phosphodiester bonds typical of nucleotides and nucleosides, and instead contains a subunit with a ring nitrogen with coupling through the ring nitrogen. In another embodiment, the antisense oligomer is a substantially uncharged phosphorodiamidate morpholino oligonucleotide (PMO). In yet another embodiment, the antisense oligomer is a phosphorothioate 2'-O-methyl oligoribonucleotides (PSO).

FIGS. 6A-6D show examples of subunits and linkages of morpholino oligomers. Morpholino oligomers afford high target binding affinity for RNA targets and are resistant to degradation by nucleases. Binding of a morpholino oligomer to a target has been shown to give strong inactivation, due to the greater binding affinity, and because the oligomer-target duplex is not susceptible to duplex unwinding mechanisms in the cell. In therapeutic applications involving cellular uptake of the antisense compound, an uncharged morpholino polymer is more efficiently transported into cells than are oligomers with charged backbones. The structures shown in FIGS. 6A-6D are linked together by phosphorus-containing linkages, one to three atoms long, joining the morpholino nitrogen of one subunit to the 5' exocyclic carbon of an adjacent subunit. $P_i$ and $P_j$ are purine or pyrimidine base-pairing moieties effective to bind, by base-specific hydrogen bonding, to a base in a polynucleotide. The purine or pyrimidine base-pairing moiety is typically adenine, cytosine, guanine, uracil, thymine, or inosine. In one embodiment, the morpholino oligomer includes subunit structures shown in FIG. 6B linked together by phosphorodiamidate linkages, joining the morpholino nitrogen of one subunit to the 5' exocyclic carbon of an adjacent subunit. The atom $Y_1$ linking the 5' exocyclic morpholino carbon to the phosphorus group may be sulfur, nitrogen, carbon, or oxygen. The X moiety pendant from the phosphorus is any stable group which does not interfere with base-specific hydrogen bonding. The X group may include fluoro, alkyl, alkoxy, thioalkoxy, and alkyl amino, including cyclic amines, all of which can be variously substituted, as long as base-specific bonding is not disrupted. Alkyl, alkoxy, and thioalkoxy preferably include 1-6 carbon atoms. Alkyl amino preferably refers to lower alkyl ($C_1$ to $C_6$) substitution, and cyclic amines are preferably 5- to 7-membered nitrogen heterocycles optionally containing 1-2 additional heteroatoms selected from oxygen, nitrogen, and sulfur. The Z is sulfur or oxygen. In another embodiment, the morpholino oligomer is a PMO and includes subunit structures shown in FIG. 6B where X is selected from the amino acid groups $NH_2$, NHR, or $NR_2$, Y is oxygen, Z is oxygen, and $P_i$ and $P_j$ are purine or pyrimidine base-pairing moieties effective to bind, by base-specific hydrogen bonding, to a base in a polynucleotide. In another embodiment, the oligomer includes an alternate phosphorodiamidate linkage, where in the subunit structures shown in FIG. 6B, X is lower alkoxy, such as methoxy or ethoxy, Y is NH or NR, R is lower alkyl, and Z is oxygen.

Two mechanisms of action of antisense oligomers on target nucleic acid molecules have been proposed for inhibiting expression. One mechanism of action of the antisense oligomer is steric blocking, in which the antisense oligomer binds to the target nucleic acid, such as the AUG start site of the mRNA, to prevent the binding of ribosomes to the target nucleic acid. Oligonucleotides belonging to the class of steric blockers include alpha anomer oligonucleotides, methylphosphonates, morpholino oligonucleotides, PNA, and certain 2'-O-allyl or 2'-O-alkyl modified oligonucleotides. Another mechanism of action of the antisense oligomer is by disrupting the nucleic acid function by enzymatic cleavage of the targeted RNA by intracellular ribonuclease H (RNase H). The antisense oligomer hybridizes with the targeted RNA forming a heteroduplex between the oligonucleotide and the RNA. The duplex activates RNase H to cleave the RNA strand, thus destroying the normal function of the RNA. Oligonucleotides belonging to the class of RNase H include phosphorothioates, phosphotriesters, and phosphodiesters. Therefore, the antisense oligomer blocks or inhibits the production of CYP3A5.

Table 2 compares representative dose and pharmacokinetics (PK) of several oligomer chemistries. Table 2 shows a narrow range in total body clearance independent of oligomer chemistry. See also Iversen (*J Drug Disc Dev Deliv* 3(2):1022, 2016). A similar PK behavior is anticipated with the chemistry approaches disclosed for the present invention, though as noted elsewhere herein the actual dosages useful for treatment are lower because of the specific characteristics of the antisense molecules and the target gene (CYP3A5) that is being suppressed.

Figure 7A:
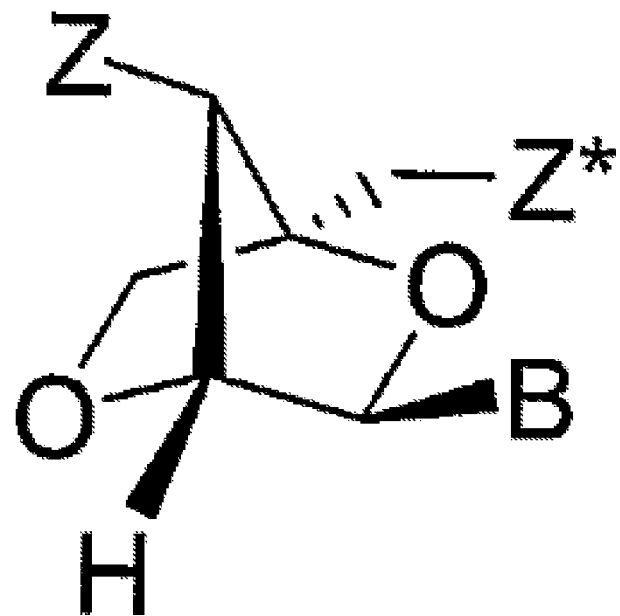
FIGS. 7A-7B illustrate nucleotide formulas for locked nucleic acid nucleotides and locked nucleic acid analog nucleotides.

FIG. 7A shows a formula for LNA nucleotides. In FIG. 7A, "B" is a nucleobase. Nucleobases include naturally occurring nucleobases as well as non-naturally occurring nucleobases. Z* includes an internucleoside linkage or a terminal group. The internucleoside linkage Z* means an internucleoside linkage to a succeeding nucleotide/nucleoside. Z is selected from a bond to the internucleoside linkage of a preceding nucleotide/nucleoside and a terminal group, provided that only one of Z and Z* can be a terminal group. Z* is a terminal group if the NLA the LNA nucleotide is the 5'-terminal nucleotide of the oligomeric compound. Z is a terminal group if the LNA nucleotide is the 3'-terminal nucleotide of the oligomeric compound. An LNA nucleotide can also include locked nucleic acids with other furanose or other sugars or with a different monomer formulation, including 2'-O,3' linked and 3'-O,4' linked, 1'-O,3' linked, 1'-O,4' linked, 3'-O,5' linked, 2'-O,5' linked, 1'-O,2' linked bicyclonucleosides, and other monomer formulations.

Figure 7B:
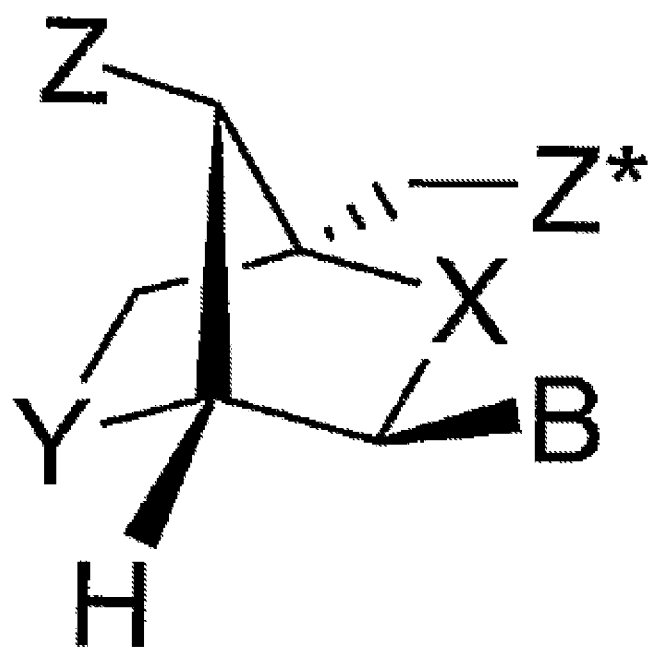

FIG. 7B shows a formula for LNA analogue nucleotides. X and Y are independently selected from —O—, —S—, —N(H)—, —N(R)—, —$CH_2$— or —C(H)=, $CH_2$—O—, —$CH_2$—S—, —$CH_2$—N(H)—, —$CH_2$—N(R)—, —$CH_2$—$CH_2$— or —$CH_2$—C(H)=, —CH=CH—. R is selected from hydrogen and $C_{1-4}$-alkyl. B, Z*, and Z are selected similarly to LNA nucleotides described with respect to FIG. 7A, provided that in the formula of FIG. 7B, the X and Y are not both oxygen.

In one embodiment, the oligonucleotides comprise LNA or LNA analog nucleotides in combination with nucleotides that are not LNA nucleotides. Such nucleotides include, for example, deoxyribonucleotides (DNA nucleotides), ribonucleotides (RNA nucleotides), nucleotide derivatives, nucleotide analogues other than LNA, and PNA units. The nucleotide analogues and derivatives include nucleotides with modified backbones or non-natural nucleoside linkages, nucleotides containing base modifications, and nucleotides containing substituted sugar moieties or sugar mimetics. Other examples of compounds useful with the present invention include oligonucleotides containing modified backbones or non-natural internucleoside linkages. Oligonucleotides having modified backbones include those that

TABLE 2

| Chemistry Class | Preclinical Efficacy Dose (mg/kg) | Clinical Efficacy Dose (mg/kg/day) | Dose Limitations (mg/kg) | Comparative Clearance Data |
|---|---|---|---|---|
| POO 2'-H | 5 to 10 | 1.5 to 5 | 2.4 to 40 | Terminal half-life: 1-2 Days |
| POO 2'-OH | 0.5 to 5 | 0.5 to 1.5 | 1.5 to 10 | Clearance: 1.5 mL/min*kg |
| | | | | Clearance: 1.4 mL/min*kg |
| PSO 2'-H | 0.6 to 30 | 1.5 to 6.0 | 2 to 6 | Clearance: 1.6 mL/min*kg |
| PSO 2'-OMe | 25 to 100 | 0.9 to 8.5 | 3 to 6 | Clearance: 1.1 mL/min*kg |
| PSO 2'-MOE | 10 to 25 | 1.5 | 2.8 to 14 | Terminal Half-life: 22-51 Days |
| | | | | Clearance: 0.9 mL/min*kg |
| PSO Conf-Constrained | 0.3 to 30 | 0.5 to 1.5 | | Terminal Half-life: 21 Days |
| | | | | Clearance: 0.6 mL/min*kg |
| PMO | 10 to 100 | 4.3 to 8 | >320 | Clearance: 1.6 mL/min*kg |

FIGS. 7A-7B show nucleotide formulas for locked nucleic acids (LNA) nucleotides and LNA analogue nucleotides. The antisense oligonucleotides may comprise nucleotide units that include one or more LNA nucleotides or LNA analogue nucleotides. LNA nucleotides and LNA analogue nucleotides refer to an oligonucleotide containing one or more bicyclic, tricyclic, or polycyclic nucleoside analogues. LNA nucleotides and LNA analogue nucleotides comprise a sugar moiety to which is linked a nucleobase and an internucleoside linkage.

retain a phosphorus atom in the backbone and those that do not have a phosphorus atom in the backbone. Modified oligonucleotides that do not have a phosphorus atom in their internucleoside backbone can also be considered to be oligonucleosides.

The basis of the antisense therapy is that the nuclease-resistant oligonucleotides designed to inhibit expression of cytochrome CYP3A5 will lower blood pressure. Inhibition of CYP3A5 expression results in a reduction of the enzymatic products of CYP3A5, e.g., 6-β-cortisol and 6-β- corticosterone, which cause sodium retention in the kidney leading to volume expansion and hypertension. The synthetic nuclease-resistant oligonucleotides that are capable of inhibiting CYP3A5 expression accumulate in the proximal tubule of the kidney, which is the site of CYP3A5 synthesis. Accumulation of the oligonucleotides in the kidney is 30 to 50 times that of accumulation in the liver, and is the second highest site of oligonucleotide accumulation in the human body. Hence, an mRNA sequence-specific inhibition of CYP3A5 is achieved with a modest PMO dose (0.2-1 mg/kg/day), potentially 30 to 50 times or more lower than the standard of care for comparable morpholinos in humans, which range from approximately 10 to 100 mg/kg (see Table 2), or in other embodiments from approximately 10-30 mg/kg (Iversen, *J Drug Disc Dev Deliv* 3(2):1022 (8 pages), 2016). Further, inhibition of other cytochrome p450s in other organs, such as the liver, is not likely to occur, because oligonucleotide accumulation in other organs is lower than in the kidney. For example, an oligomer targeting CYP3A4 in the liver inhibits CYP3A5 in the kidney, even with more than four mispairing bases, due to accumulation in the kidney. By contrast, an oligomer targeting CYP3A5 in the kidney does not inhibit the closely related CYP3A4 in the liver.

The basis of embodiments of the invention, that reducing the expression of CYP3A5 results in a reduction the enzymatic products of CYP3A5 and a decrease in hypertension, is further supported by a study of heart transplant patients. Heart transplant patients treated with cyclosporine (CSA) to prevent transplant rejection frequently develop hypertension (Lustig et al., *Transplant Proc.* 19(1 Pt 2):1262-1264, 1987). The spontaneously hypertensive rat (SHR) appears to mimic the response by elevation in blood pressure following administration of CSA. CSA induces the CYP3A family in renal CYP3A, but not hepatic CYP3A in the SHR model, while administration of stannous chloride diminishes systolic blood pressure in the SHR due to depletion of renal, but not hepatic CYP3A. Administration of troleandomycin (TAO), an inhibitor of CYP3A activity, reduces systolic blood pressure (SBP) in the SHR. If TAO is administered prior to CSA in the SHR model, SBP is reduced from 179 mmHg to 139 mmHg (Watlington et al., *Am J Physiol* 262:F927-F931, 1992). CYP3A is localized to the proximal tubule of the kidney in the SHR, the synthetic site for 6-β-OH-corticosterone. SHR show elevated SBP by week 10 post-partum, in concert with excretion of 6-β-OH-corticosterone, and expression of kidney CYP3A. TAO reduces 6-β-OHase activity in the kidney from 1.9 to 0 picomoles per minute per milligram (pmol/min/mg) protein (p<0.001), but in the liver the reduction is from 5.9 to 4.1 pmol/min/mg (p<0.05) (Ghosh et al., *Biochem Pharm* 50:49-54, 1995). The animal model data in that research support the hypothesis that renal CYP3A in the rat will create 6-β-OH-corticosterone, which mediates increased tubular reabsorption of sodium leading to volume expansion and salt sensitive hypertension. Differentially expressed genes (DEG) in the kidney between Dahl salt sensitive (DS) rats and Lewis rats were recently identified using DNA microarrays (Kuang et al., *Eur Rev Med Pharmacol Sci.* 17(23):3148-3156, 2013). The results found 1264 DEGs with 1082 DEGs upregulated and 182 DEGs down regulated. The results also found CYP3A2, an ortholog to human CYP3A4, down regulated and CYP3A9, an ortholog to human CYP3A5, upregulated in the DS rats.

Figure 8:
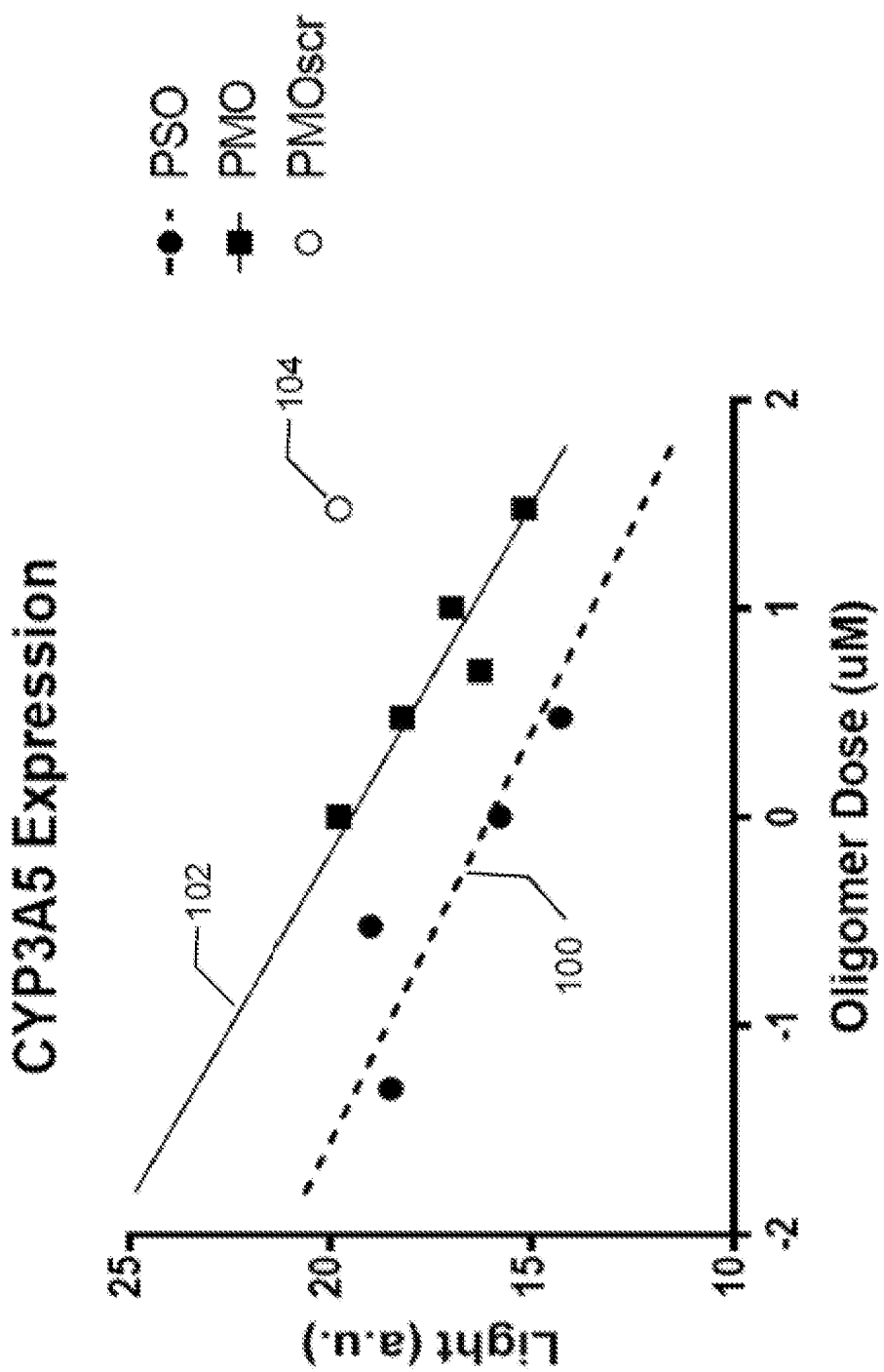
FIG. 8 illustrates results of study using antisense oligomers to reduce CYP3A5 expression. Each data point represents the mean of three independent observations. The filled circles represent data from the PSO targeting CYP3A5 and the dashed line is a regression analysis $Y=-2.54*X+16.4$, $r^2=0.7515$. The filled squares represent data from the PMO targeting CYP3A5 and the solid line is a regression analysis $Y=-2.988*X+19.48$, $r^2=0.8733$. The PMO line slope is significantly different from zero, $p=0.0199$. Finally, the open circle is the scrambled sequence control at the highest concentration which indicates no inhibition of CYP3A5 activity.

FIG. 8 shows results of a study using antisense oligomers for reducing CYP3A5 expression. Oligomers having SEQ ID NO: 1 were prepared as both PSO (purchased from Integrated DNA Technologies in Coralville, Iowa) and as PMO (purchased from GeneTools in Philomath, Oreg.). Caco-2 clone TC7 cells were used because the cells constitutively express CYP3A5 and not CYP3A4, which is key to the experimental design in that the metabolism of the substrate can only come from CYP3A5, the target of the oligomers.

A quantity of approximately 20,000/well of caco-2 clone TC7 cells were grown in a white-walled, 96-well cell culture plate, purchased from Greiner Bio-One. A dose-range of oligomer of 0.3-30 micromoles (µM) was added to the media to establish a dose-response relationship for inhibition of CYP3A5 enzymatic activity. The oligomers were allowed three days to enter cells and interact with targeted RNA. A scrambled sequence PMO (SEQ ID NO: 9) was added as a negative control. At the end of the incubation period, a biochemical luminescent assay method for measuring cytochrome P450 activity sold under the trademark CYP3A P450-GLO™ assay, LUCIFERIN-PFBE, purchased from Promega, was added in fresh media and incubated for 60 minutes at 37 degrees Celsius (° C.). The assay was followed by cell lysis via the addition of a luciferase enzyme reaction mix sold under the trade name LUCIFERIN DETECTION REAGENT (LDR). Luminescence was measured directly from the cell culture plate at 0, 15, and 30 minutes after LDR addition using a plate reader for fluorescence, absorbance, and luminescence measurements sold under the trademark SYNERGY™ HT multi-mode microplate reader, purchased from Biotek, using Promega's recommended settings.

Each data point in FIG. 8 represents the mean of three independent observations. The filled circles represent data from the PSO targeting CYP3A5. Line 100 is a regression analysis of the PSO data having a slope represented by equation (1).

$$Y=-2.54*X+16.4, r^2=0.7515 \quad (1)$$

The filled squares represent data from the PMO targeting CYP3A5. Line 102 is a regression analysis of the PMO data having a slope represented by equation (2).

$$Y=-2.988*X+19.48, r^2=0.8733 \quad (2)$$

The slope of line 102 is significantly different from zero (p=0.0199). The open circle, point 104, is the scrambled sequence control (SEQ ID NO: 9) at the highest concentration which indicates no inhibition of CYP3A5 activity. The data shown in FIG. 8 demonstrate that SEQ ID NO: 1 inhibits expression of CYP3A5.

Routes of administration of antisense oligomers include, oral and parenteral routes, such as intravenous, subcutaneous, intraperitoneal, intramuscular, and intraarterial injection, as well as inhalation and transdermal delivery. A physiologically acceptable carrier or pharmaceutically acceptable carriers is selected according to the mode of administration. Examples of pharmaceutically acceptable carriers include saline, phosphate buffered saline (PBS), water, aqueous ethanol, emulsions such as oil/water emulsions, triglyceride emulsions, wetting agents, tablets, and capsules. In one embodiment, for transdermal delivery of antisense oligomers, a pharmaceutically acceptable carrier is selected for topical administration. In another embodiment, the oligomer is a morpholino oligomer contained in a pharmaceutically acceptable carrier and is delivered orally.

The route of administration is expected to be transdermal, subcutaneous, or oral, with a feasible dose of 5-10 mg/day. Dosing is expected to be relatively low due to accumulation of oligonucleotides in the kidney and is also expected to be reducible to one dose per week. The human equivalent dose estimate for kidney-targeted CYP3A5 oligomers was derived from polycystic kidney disease mouse model data. Oligomers were used to target c-myc in C57BL/6J$^{cpk/cpk}$ autosomal recessive mouse model of disease. Dose of 10 micrograms (μg) intraperitoneally (i.p.) daily from postnatal day 7 to 20 was effective in reducing c-myc expression and kidney cyst formation. Mice were 10 g body weight so the dose received was approximately 1.0 mg/kg. If scaled (by mg/m$^2$) to HED of 0.083 mg/kg, the expected dose in a 70 kg human would be 5.8 mg/day, or 2.1 grams/year.

Accordingly, antisense oligomer compositions and methods are disclosed for selectively inhibiting CYP3A5 in the kidney for the treatment of hypertension and prevention of organ transplant rejection. The antisense oligomer is advantageous over other therapies because the antisense oligomer is both gene-specific and targets the kidney, which is the site of CYP3A5 production. Because antisense oligomers accumulate in the kidney, a more efficient dosing can be achieved. Because an antisense approach is gene-specific, the antisense oligomer is a more specific inhibitor than a substrate inhibitor. For example, the antisense oligomer does not inhibit the similar enzyme, CYP3A4, which is expressed in the liver and small intestine and metabolizes a significant amount of prescribed drugs. A patient taking other prescription drugs would be at risk of altering the prescription drug pharmacokinetics if CYP3A4 was inhibited. By inhibiting CYP3A5, but not CYP3A4, the list of contraindicated drugs can be significantly reduced for the antisense therapy. Patients can safely take, for example, immunosuppressants, with the antisense therapy, thereby reducing the likelihood or organ transplant rejection.

Further, an antisense oligomer inhibits production of the CYP3A5 protein altogether. Blocking the synthesis of the protein is a more efficient approach to inhibiting the action of CYP3A5. Problems with a substrate inhibitor, such as reactive byproducts formed by blocking the action of the CYP3A5 later in the metabolic reaction, are avoided with an antisense inhibitor. CYP3A5 also inactivates vitamin D, so reducing CYP3A5 expression would reduce the inactivation of vitamin D and improve vitamin D deficiency.

EXAMPLE 1

Salt Restoration of CYP3A5 Expression in a CYP3A5*3/*3 Genotype.

Figure 9:
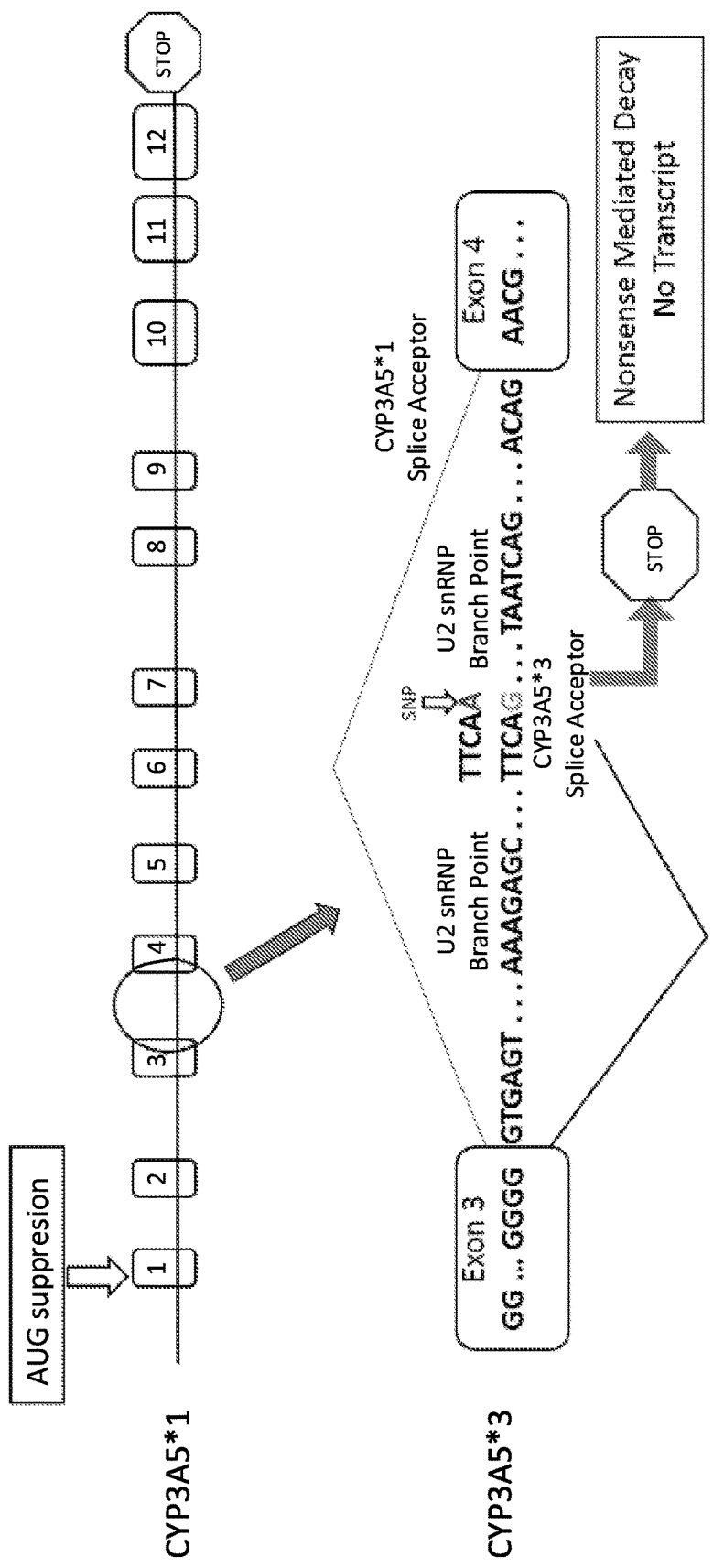
FIG. 9 illustrates cytochrome P450 3A5 (CYP3A5) transcript variants resulting from intronic SNP A1598G creates a cryptic splice acceptor site.

A human embryonic kidney cell line, HEK293 (American Type Culture Collection CRL-15730), was derived from the epithelial layer of a human kidney. Referring now to FIG. 9, analysis of the CYP3A5 gene reveals the genome of HEK293 is homozygous and encodes the CYP3A5*3/*3 variant form of CYP3A5 exemplified by the CAG sequence (rs776746 or 6986A>G) in intron 3 compared to the CAA sequence found in the CYP3A5*1 variant. This single nucleotide polymorphism appears to create a cryptic splice acceptor site in intron 3 that can lead to nonsense mediated decay (NMD) of the CYP3A5 transcript. The degradation of the CYP3A5 transcript is consistent with virtually no detectable CYP3A5 mRNA, protein or enzymatic activity.

Figure 10A:
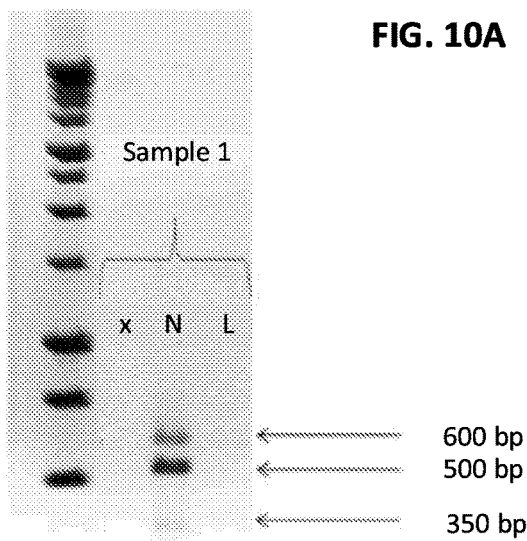
FIG. 10A is a photograph of a gel showing PCR amplification of CYP3A5 mRNA with FP-AAATTTGGCGGTG-GAAAC (SEQ ID NO: 10) and RP-GACAGGCTTGC-CTTTCTCTG (SEQ ID NO: 11) revealing no detectable transcript in media only cells (lane x), exon 4 inclusion and stable CYP3A5 496 bp product in cells treated with 500 mOsmol NaCl (lane N), and no transcript in cells treated with 500 mOsmol LiCl (lane L).
Figure 10B:
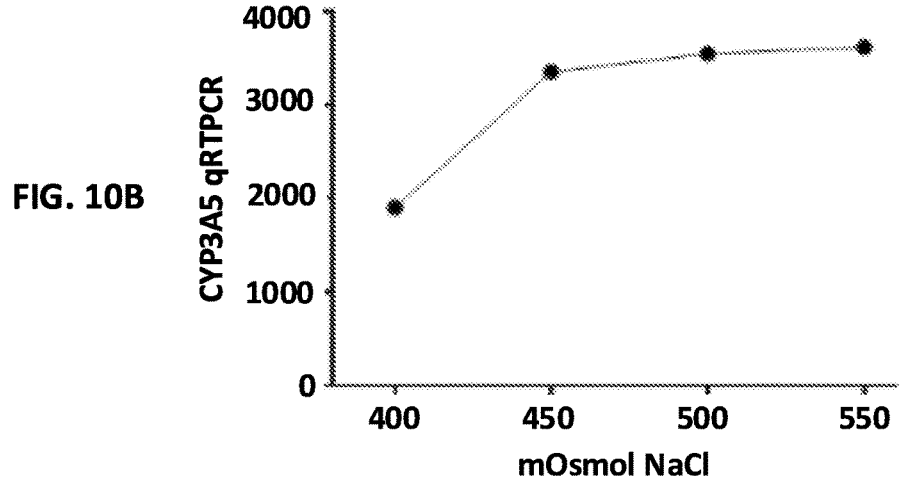
FIG. 10B is a graph showing qRT PCR copies of CYP3A5 with increasing mOsmol NaCl up to 550 mOsmol.
Figure 10C:
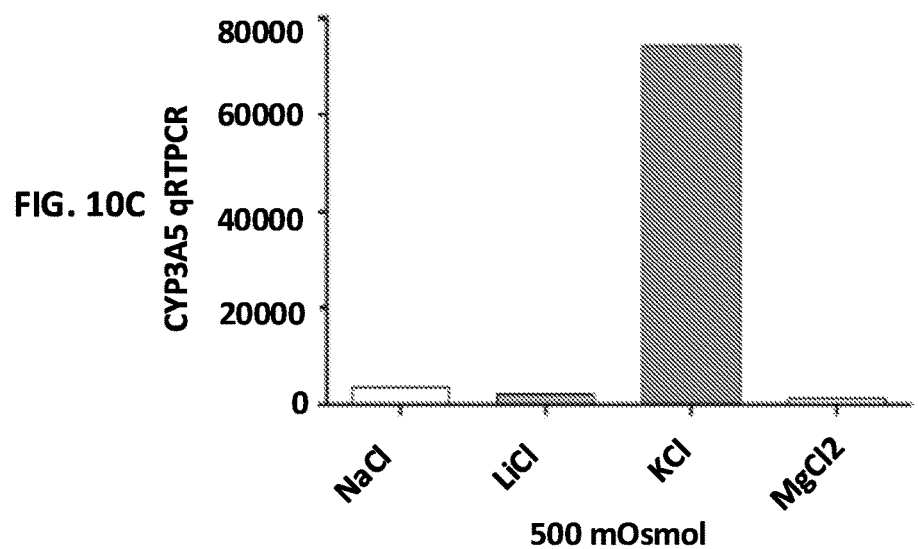
FIG. 10C is a graph comparing different salt treatment of HEK293 cells at 500 mOsmol and resulting levels of stable CYP3A5 mRNA.

Referring now to FIG. 10, cultivation of the HEK293 cells in hyperosmotic concentrations of sodium chloride (500 milliosmoles (mOsm) NaCl) results in a detectable CYP3A5 mRNA and protein. FIG. 10A: left lane is a molecular weight marker lane, lane indicated by the "x" is an untreated control sample with undetectable CYP3A5 transcript, lane "N" is a hyperosmotic NaCl treated sample and shows a prominent CYP3A5 transcript band at 500 bp, lane "L" is a hyperosmotic LiCl treated sample with no detectable CYP3A5 transcript. Induction of CYP3A5 transcript is observed at 400 mOsm and complete induction is observed at 450 mOsm NaCl (FIG. 10B). The salt restoration of CYP3A5 mRNA in HEK293 cells is over 25 times greater when hyperosmotic concentrations of potassium chloride are employed (KCl), indicating the expressed mRNA is not due to osmolarity induction of the TonE promoter (FIG. 10C). Inspection of the intron sequence flanking the 6986A>G SNP reveals a potential guanine tetrad structure referred to as a G-quartet or G4. Further, G4 structures are most readily formed in the presence of potassium ions. Since G4 structures are disrupted by lithium ions, studies were conducted in HEK293 cells with up to 500 mOsm lithium chloride (LiCl) which reveal no restoration of CYP3A5 mRNA confirming that osmolarity is not responsible for CYP3A5 expression and the G4 structure is acting as a structural splicing switch that will shift the splice site from the intron 3 CAG site to the exon 4 CAG splice acceptor site. These observations can explain why people with CYP3A5*3/*3 variants can still express CYP3A5 protein and its resulting enzymatic activity.

Figure 11:
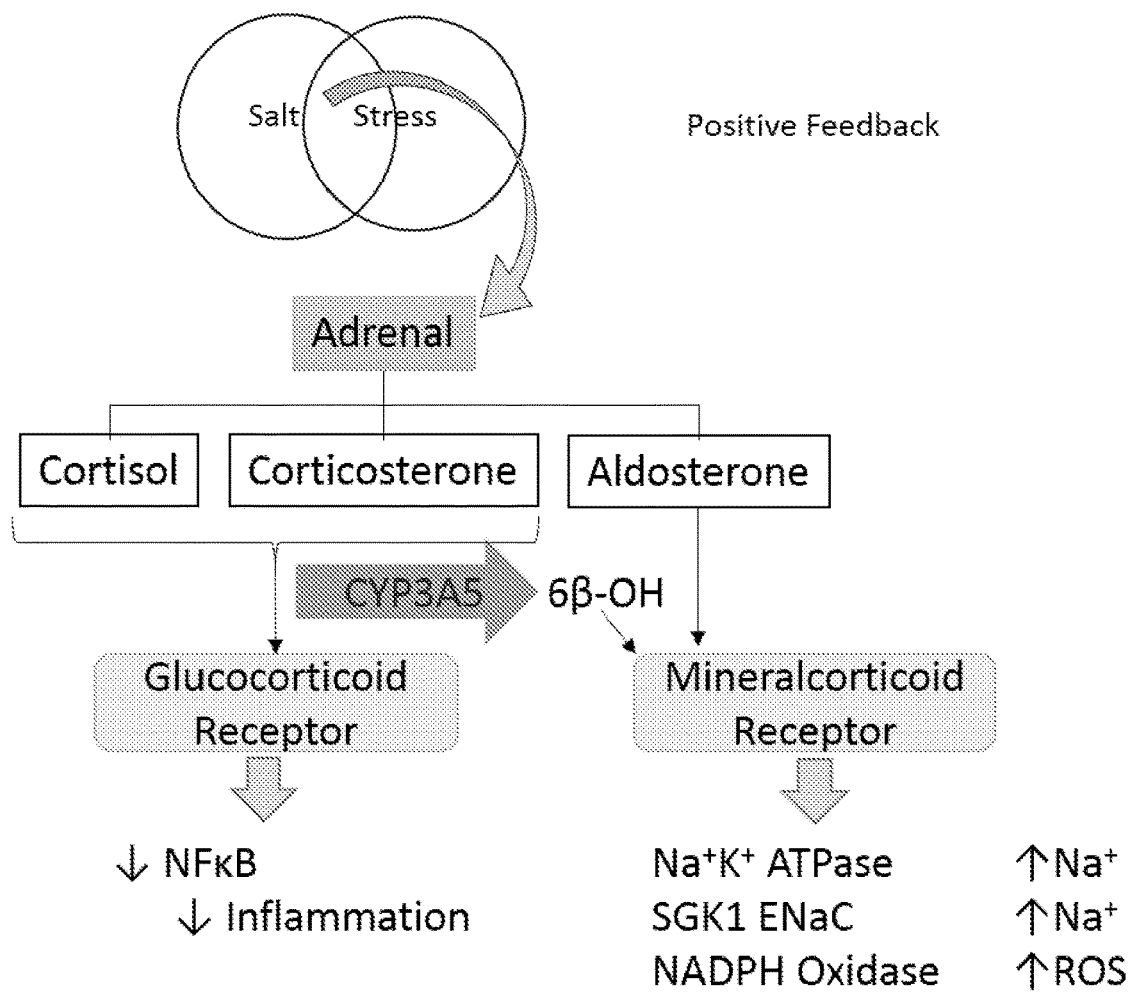
FIG. 11 illustrates cytochrome P450 3A5 (CYP3A5) shifts stress response to hypertensive phenotype. The large block arrow indicates the activity of CYP3AF in producing hydroxyl products of cortisol and corticosterone.
Figure 12A:
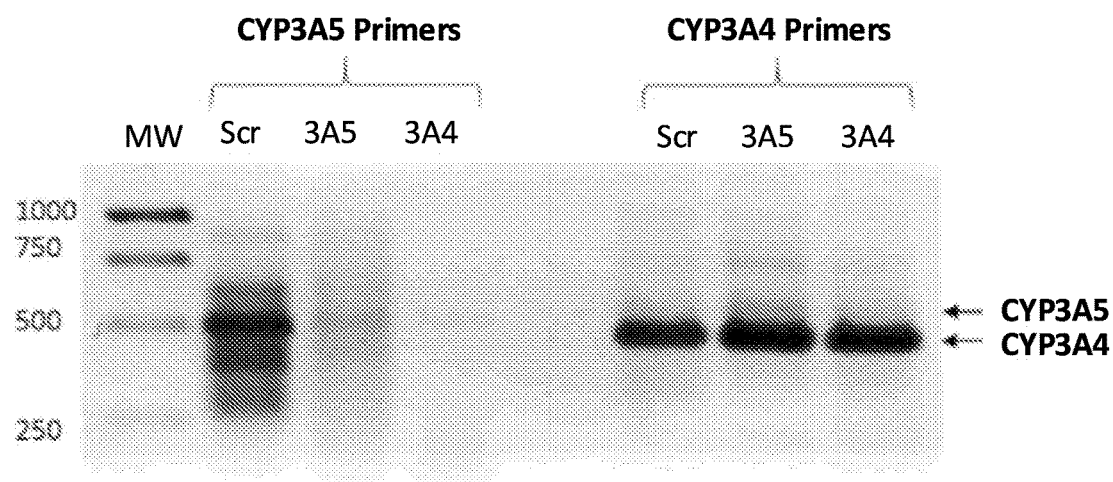
FIG. 12A-12B illustrate analysis of the expression of CYP3A5-AUG SEQ ID NO: 1 in TC7 Caco-2 Cells by Endpoint PCR (FIG. 12A).
Figure 12B:
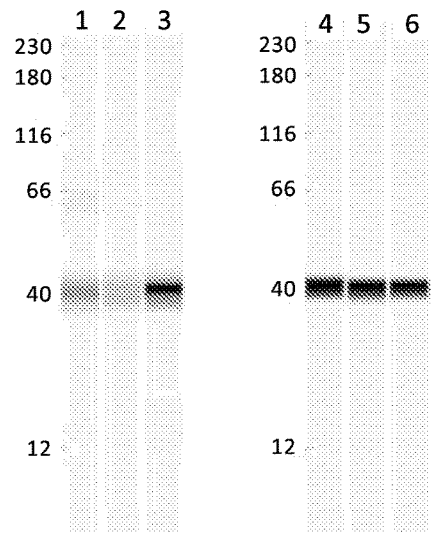
Figure 12C:
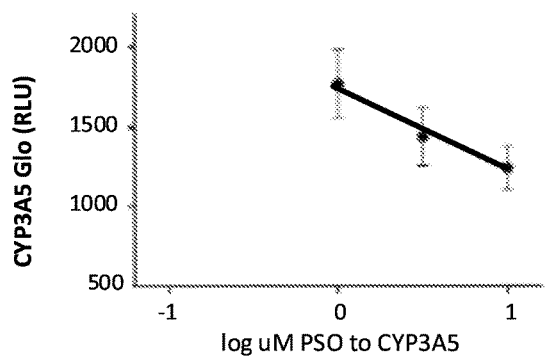
FIG. 12C-12F are a series of graphs showing CYP3A5 enzyme activity after treatment with the indicated oligonucleotide, using Promega P450glo substrates.
Figure 12D:
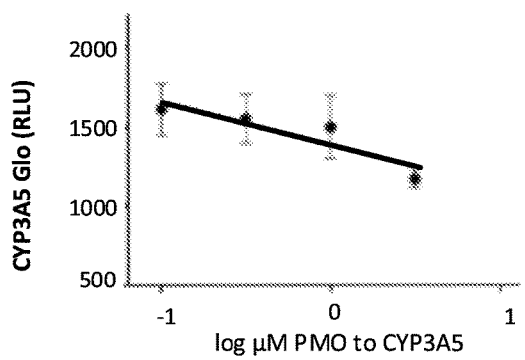
Figure 12E:
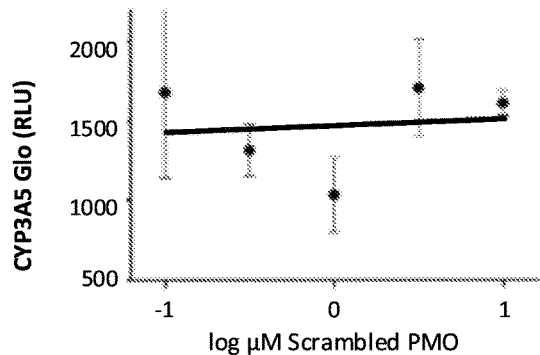
Figure 12F:
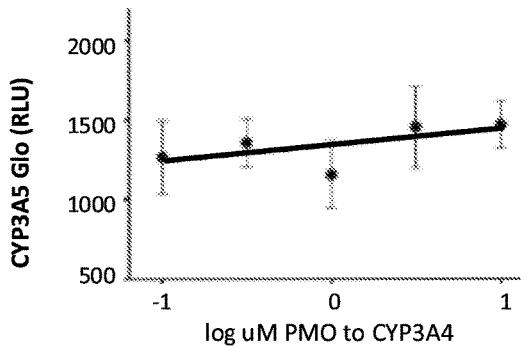

Referring now to FIG. 11, stress leads to enhanced activity in the hypothalamic-pituitary axis leading to release of adrenocorticotropic hormone (ACTH). The effect of ACTH on the adrenal gland is to enhance synthesis of cortisol that is converted to aldosterone which binds to the mineralocorticoid receptor resulting in salt retention through the action of a Na+K+ ATPase and the SGK1 ENaC channel by the proximal tubule of the kidney. However, the adrenal gland also enhances production of cortisone and corticosterone in response to ACTH. The action of CYP3A5 is to convert cortisone and corticosterone to 6β-hydroxylated products which are also ligands for the mineralocorticoid receptor. In this way, CYP3A5 diverts the actions of cortisone and corticosterone from activation of the glucocorticoid receptor which is generally an anti-inflammatory effect to an enhanced mineralocorticoid effect. The amplified salt retention observed can explain why individuals with CYP3A5*3 variant can develop stress induced hypertension in addition to CYP3A5*1 individuals.

EXAMPLE 2

CYP3A5 Sequence-specific Inhibition but not CYP3A4 by SEQ ID NO: 1

Antisense oligomers are shown in Table 1. The oligomer CYP3A5-AUG (SEQ ID NO: 1) is a 23-mer having 100% complementarity to the region containing the AUG start codon in the human CYP3A5 mRNA. Referring now to FIG. 12, synthetic oligomers having SEQ ID NO: 1, were prepared as both PSO, purchased from Integrated DNA Technologies (Coralville, Iowa), and as PMO, purchased from GeneTools (Philomath, Oreg.). Caco-2 clone TC7 cells were used because the cells constitutively express CYP3A5 and not CYP3A4, which is key to the experimental design in that the metabolism of the substrate can only come from CYP3A5, the target of the oligomers. A quantity of approximately 20,000/well of caco-2 clone TC7 cells were grown in a white-walled, 96-well cell culture plate, purchased from Greiner Bio-One. A dose-range of oligomers of 0.3-30 micromoles (μM) was added to the media to establish a dose-response relationship for inhibition of CYP3A5 enzymatic activity. The oligomers were allowed three days to enter cells and interact with targeted RNA. A scrambled sequence PMO (SEQ ID NO: 9) was added as a negative control. At the end of the incubation period, a biochemical luminescent assay method for measuring cytochrome P450 activity sold under the trademark CYP3A P450-GLO™ assay, LUCIFERIN-PFBE, purchased from Promega, was added in fresh media and incubated for 60 min at 37 degrees Celsius (° C.). The assay was followed by cell lysis via the addition of a luciferase enzyme reaction mix sold under the trade name LUCIFERIN DETECTION REAGENT (LDR). Luminescence was measured directly from the cell culture plate at 0, 15, and 30 minutes after LDR addition using a plate reader for fluorescence, absorbance, and luminescence measurements sold under the trademark SYNERGY™ HT multi-mode microplate reader, purchased from Biotek, using Promega's recommended settings.

EXAMPLE 3

Oligomers Targeting Intron 3 Influence Expression of CYP3A5*3

HEK293 cells were exposed to oligomer CYP3A5*3 (SEQ ID NO: 3) which was designed to bind to the cryptic splice acceptor site in intron 3 of CYP3A5*3 and prevent splicing at that site resulting in correct splicing to the splice acceptor of exon 4. Exposure to this oligomer in HEK293 cells for 48 hours led to expression of CYP3A5 mRNA and protein confirming the proposed action of this 6986A>G mutation as an alternate splice acceptor site. Further, addition of LiCl to HEK293 cells exposed to CYP3A5*3 oligomer prevented the mRNA expression confirming the location of the G4 structure near this SNP.

Referring now to FIG. 13, exposure of the HEK293 cells to the oligomer CYP3A5 G4 disrupter (SEQ ID NO: 4), which is designed to hybridize to the intron sequence involved in the formation of the G4 structure, do not express CYP3A5 mRNA or protein. Co-administration of KCl to HEK293 cells with the CYP3A5 G4 disrupter prevented the enhanced expression of CYP3A5 mRNA which confirms the role of the G4 structure in switching splicing from 6986A>G to the splice acceptor of exon 4. This also establishes the potential therapeutic use of the CYP3A5 G4 disruptor (SEQ ID NO: 4) in treating potassium induced hypertension observed in Bartter's and Gordon's syndrome.

EXAMPLE 4

Oligomers Targeting Exon 4 Manipulate Expression of CYP3A5*3.

Referring now to FIG. 14, the antisense oligomers identified as CYP3A5dex4(−3,19) (SEQ ID NO: 5), CYP3A5dex4(−9,16) (SEQ ID NO: 6), CYP3A5dex4(−17, 5) (SEQ ID NO: 7), and CYP3A5dex4(+94,118) (SEQ ID NO: 7) are 100% complementary to the human CYP3A5 exon 4 region in the pre-mRNA and were designed to induce exclusion of exon 4. The alignment of the oligomers with Exon 4 is indicated in FIG. 14A. FIG. 14B shows a paradoxical inclusion of exon 4 in the presence of CYP3A5dex4(−3,19) (SEQ ID NO: 5), CYP3A5dex4(−9, 16) (SEQ ID NO: 6), CYP3A5dex4(−17,5) (SEQ ID NO: 7), and CYP3A5dex4(+94,118) (SEQ ID NO: 8) oligomers, which are thought to be the result of the oligomer masking the exon junctional complex (EJC) and thus preventing NMD in the CYP3A5*3 transcript and the most efficient NMD blocker is CYP3A5dex4(−3,19) (SEQ ID NO: 5); FIG. 14C confirms an increase in CYP3A5 transcript copy number using quantitative PCR again indicating the most effective oligomer is CYP3A5dex4(−3,19) (SEQ ID NO: 5); FIG. 14D is a western blot using an antibody directed at CYP3A5 protein which shows a protein with correct molecular weight with CYP3A5dex4(+94,118), while the three oligomers targeting the exon 4 splice acceptor region result in CYP3A5 protein aggregates. Since the CYP3A5*3 transcript is splicing into intron 3, the aggregate protein products reflect novel CYP3A5 protein interactions due to inclusion of out of frame amino acids.

Figure 15:
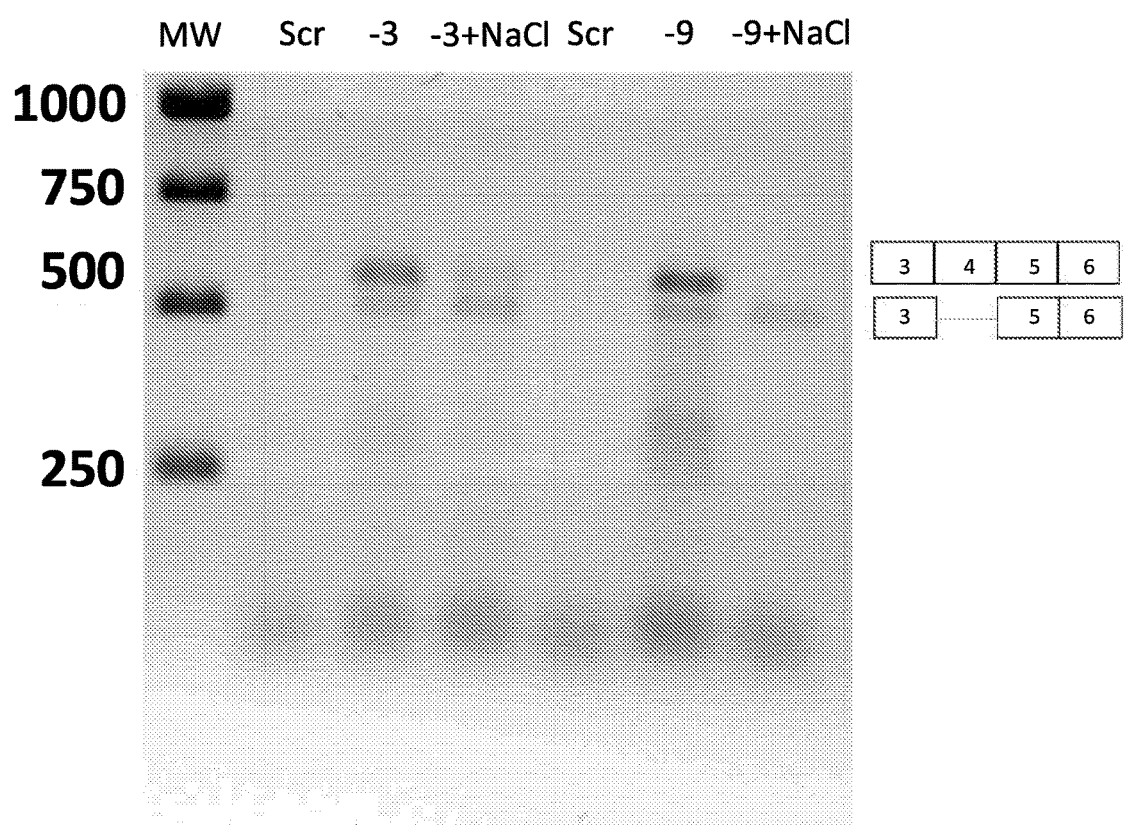
FIG. 15 is a photo of a gel that illustrates expression of CYP3A5 transcript in HEK293 cells incubated with SEQ ID NO: 5 and 6, indicating skipping of exon 4 when salt is present. Left lane: molecular weight markers. Scr Lane represents cells treated with a scrambled control oligomer (SEQ ID NO: 9) showing undetectable CYP3A5 transcript. −3 lane shows the paradoxical inclusion of exon 4 in the presence of the CYP3A5dex4(−3,19) oligomer (SEQ ID NO: 5), which is thought to be the result of the oligomer masking the exon junctional complex (EJC) and thus preventing NMD in the CYP3A5*3 transcript, −2+NaCl lane shows CYP3A5dex4(−3,19) (SEQ ID NO: 5)-induced skipping of exon 4, which is now in frame due to the salt induced formation of the G4 structure that shifts splicing to exon 4 (loss of exon 4 results in an mRNA that is out of frame and degradation by NMD). −9 lane is similar to the −3 lane with the exception that CYP3A5dex4(−9,16) oligomer (SEQ ID NO: 6) was utilized. −9+NaCl lane is similar to −3+NaCl lane with the exception that CYP3A5dex4(−9,16) oligomer (SEQ ID NO: 6) was evaluated.

Referring now to FIG. 15, the antisense oligomers identified as CYP3A5dex4(−3,19) (SEQ ID NO: 5) and CYP3A5dex4(−9,16) (SEQ ID NO: 6) are 100% complementary to the human CYP3A5 exon 4 region in the pre-mRNA and were designed to induce exclusion of exon 4. FIG. 15 Left lane; molecular weight markers; Scr Lane represents cells treated with a scrambled control oligomer and undetectable CYP3A5 transcript; −3 lane shows a paradoxical inclusion of exon 4 in the presence of the CYP3A5dex4(−3,19) oligomer which is thought to be the result of the oligomer masking the exon junctional complex (EJC) and thus preventing NMD in the CYP3A5*3 transcript; −2+NaCl lane shows CYP3A5dex4(−3,19) induced skipping of exon 4 which is now in frame due to the salt induced formation of the G4 structure that shifts splicing to exon 4 (Loss of exon 4 results in an mRNA that is out of frame and degradation by NMD). −9 lane is similar to the −3 lane with the exception that CYP3A5dex4(−9,16) (SEQ ID NO: 6) oligomer sequence was utilized, −9+NaCl lane is similar to −3+NaCl lane with the exception that CYP3A5dex4(−9,16) (SEQ ID NO: 6) oligomer was evaluated. Co-administration of these oligomers with 500 mOsm NaCl to HEK293 cells induces exclusion of exon 4 and resultant reduction in CYP3A5 mRNA and protein. These oligomers effectively convert CYP3A5*1 genotypes to a CYP3A5*3 phenotype, and these studies confirm the potential utility of exon 4 exclusion in the treatment of hypertension.

Referring now to FIG. 16, a higher order structure in intron 3 known as a G-quartet or G4 structure acts as a potassium sensitive switch leading to a shift in splicing from the CYP3A5*3 CAG site to the CAG site at the exon 4 splice acceptor functionally converting a CYP3A5*3 into a CYP3A5*1 phenotype (FIG. 16A and FIG. 16C). FIG. 16B shows the increase in number of CYP3A5*3 transcripts when HEK293 cells are incubated with KCl in the presence of a scrambled oligomer control, but when cells are incubated with the CYP3A5 G4 disrupter oligomer (SEQ ID NO: 4), the KCl effect is blocked due to the oligomer disruption of the G4 structure and the splicing switch to the exon 4 splice acceptor effectively blocking the functional conversion of the CYP3A5*3 to a CYP3A5*1 phenotype.

Figure 17:
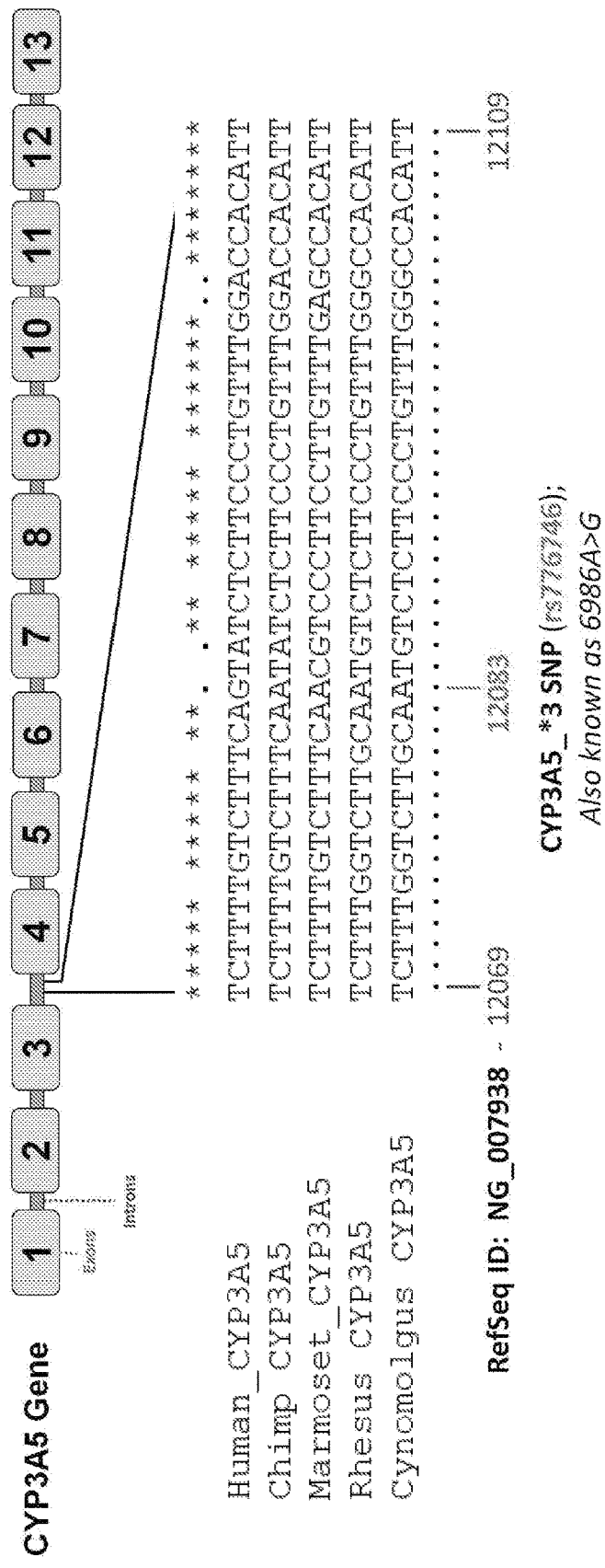
FIG. 17 is a DNA sequence Alignment of the CYP3A5*3 polymorphism in primates. In order (top to bottom), the aligned sequences are from Human CYP3A5 (SEQ ID NO: 12; positions 1655 to 1695), Chimpanzee CYP3A5 (SEQ ID NO: 13; positions 1656 to 1696), Marmoset CYP3A5 (SEQ ID NO: 14; positions 1620 to 1660), Rhesus monkey CYP3A5 (SEQ ID NO: 15; positions 1650 to 1690), and Cynomolgus monkey CYP3A5 (SEQ ID NO: 16; positions 1688 to 1728).

FIG. 17 shows the results of DNA sequence alignment of the CYP3A5*3 polymorphism in primates. Genetic polymorphisms within Intron 3 of the human CYP3A5 gene may reduce susceptibility to salt- and stress-induced hypertension. Populations that carry at least one allele of the CYP3A5*3 SNP (CAA to CAG; rs776746; 6986A>G), which generates an improperly spliced transcript subject to NMD, are less likely to express functional CYP3A5, and are thus less responsive to the autocrine mineralcorticoid response potentiated by the renal formation of 6-β-cortisol and 6-β-corticosterone. The CYP3A5*3 mutation is common in many Caucasians, and may represent a recent genetic adaptation to human migration, and changing salt availability in the diet. Our proprietary RTE technology can modulate the expression of the wild-type CYP3A5*1 phenotype that is common in in many dark-skinned people, by converting their functional CYP3A5 profile into an inactive CYP3A5*3 phenotype, safely and on-demand, using our renal-specific targeting strategy. In order, the aligned sequences are from Human CYP3A5 (SEQ ID NO: 12; positions 1655 to 1695), Chimpanzee CYP3A5 (SEQ ID NO: 13; positions 1656 to 1696), Marmoset CYP3A5 (SEQ ID NO: 14; positions 1620 to 1660), Rhesus monkey CYP3A5 (SEQ ID NO: 15; positions 1650 to 1690), and Cynomolgus monkey CYP3A5 (SEQ ID NO: 16; positions 1688 to 1728).

Figure 18:
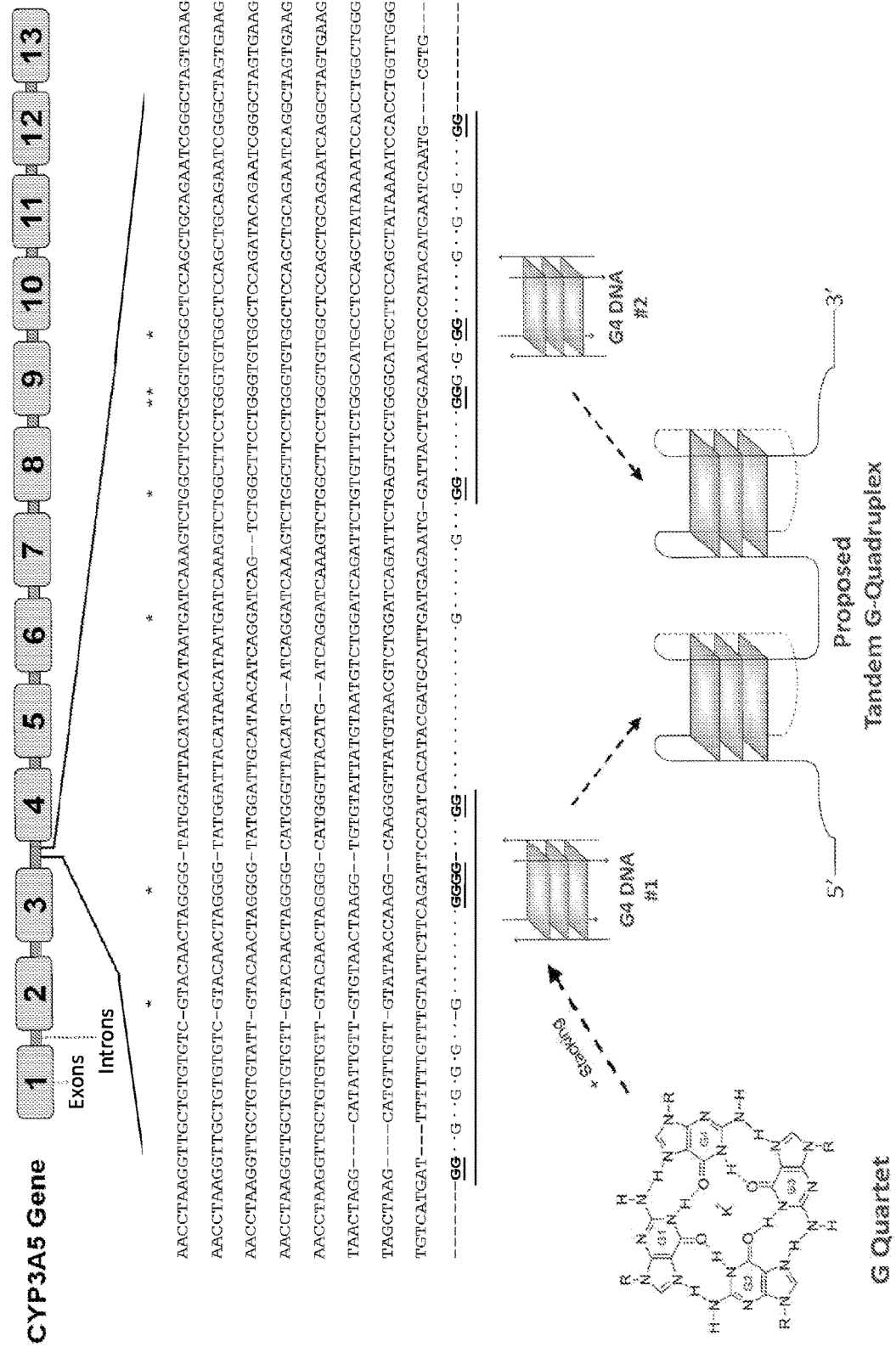
FIG. 18 illustrates quadruplex forming G-rich sequences (QGRS) in CYP3A5 and related sequences. We used the QGRS Mapper (at bioinformatics.ramapo.edu/QGRS/), a web-based server that predicts to probe the non-coding nucleotide region of CYP3A5 intron 3, in proximity to the CYP3A5*3 SNP polymorphism. In order (top to bottom), the aligned sequences are from Human CYP3A5 (SEQ ID NO: 12; positions 1769 to 1877); Chimpanzee CYP3A5 (SEQ ID NO: 13; positions 1770 to 1878), Marmoset CYP3A5 (SEQ ID NO: 14; positions 1734 to 1840), Rhesus monkey CYP3A5 (SEQ ID NO: 15; positions 1764 to 1870), Cynomolgus monkey CYP3A5 (SEQ ID NO: 16; positions 1802 to 1908), rat CYP3A9 (SEQ ID NO: 17; positions 2099 to 2202), mouse CYP3A13 (SEQ ID NO: 18; positions 1765 to 1868), and zebrafish CYP3C1 (SEQ ID NO: 19; positions 1655 to 1754), as well as the putative G4 motifs found in this alignment; RefSeq ID: NG_007938—positions 12183 to 12291.

The QGRS Mapper, a web-based server that predicts quadruplex forming G-rich sequences (QGRS) (available online at bioinformatics.ramapo.edu/QGRS/), was used to probe the non-coding nucleotide region of CYP3A5 intron 3, in proximity to the CYP3A5*3 SNP polymorphism. Our search identified the signature of a highly conserved tandem G4 quadruplex positioned approximately 100 bases after the SNP site (FIG. 18). RNA G-quadruplexes are known to regulate polyadenylation and splicing events in mammalian transcripts, and we have evidence suggesting this tandem motif in intron 3 of CYP3A5 functions as a potassium ion (K+) sensor modulating CYP3A5 transcript splicing and stability. Our RTE technology can manipulate the ion-sensing structural components of the tandem G4 structure, providing an alternative therapeutic paradigm for modulating renal CYP3A5 activity. In FIG. 18, the aligned sequences are from Human CYP3A5 (SEQ ID NO: 12; positions 1769 to 1877); Chimpanzee CYP3A5 (SEQ ID NO: 13; positions 1770 to 1878), Marmoset CYP3A5 (SEQ ID NO: 14; positions 1734 to 1840), Rhesus monkey CYP3A5 (SEQ ID NO: 15; positions 1764 to 1870), Cynomolgus monkey CYP3A5 (SEQ ID NO: 16; positions 1802 to 1908), rat CYP3A9 (SEQ ID NO: 17; positions 2099 to 2202), mouse CYP3A13 (SEQ ID NO: 18; positions 1765 to 1868), and zebrafish CYP3C1 (SEQ ID NO: 19; positions 1655 to 1754), as well as the putative G4 motifs identified in this alignment; RefSeq ID: NG_007938—positions 12183 to 12291. Any oligomer that disrupts one of these predicted G4 motifs is specifically considered as useful in influencing CYP3A5 activity as described herein.

While one or more embodiments of the present invention have been illustrated in detail, the skilled artisan will appreciate that modifications and adaptations to those embodiments may be made without departing from the scope of the present invention as set forth in the following claims.

What is claimed is:

1. A method of treating hypertension in a subject, comprising administering to a subject with elevated systolic blood pressure (SBP), a non-naturally occurring antisense oligomer specifically targeted to cytochrome CYP3A5 mRNA and effective to reduce expression of cytochrome CYP3A5 enzyme.

2. The method of claim 1, wherein the antisense oligomer comprises the sequence of SEQ ID NO: 1, SEQ ID NO: 2, SEQ ID NO: 3, SEQ ID NO: 4, SEQ ID NO: 5, SEQ ID NO: 6, or SEQ ID NO: 7.

3. The method of claim 1, wherein the antisense oligomer comprises a phosphorodiamidate morpholino oligonucleotide.

4. The method of claim 1, wherein the antisense oligomer comprises a phosphorothioate 2'-O-methyl oligoribonucleotide.

5. The method of claim 1, wherein the antisense oligomer comprises a locked nucleic acid nucleotide or locked nucleic acid analog nucleotide.

6. The method of claim 1, wherein the antisense oligomer is administered transdermally to the subject.

7. The method of claim 1, wherein the subject has a SBP of greater than 140 millimeters of mercury (mm Hg) and a diastolic blood pressure (DBP) of greater than 90 mm Hg.

8. The method of claim 1, wherein the subject has a homozygous CYP3A5*1/*1 genotype, a homozygous *3/*3 genotype, or a heterozygous CYP3A5*1/*3 genotype.

9. The method of claim 8, wherein the subject has a homozygous CYP3A5*1/*1 genotype.

10. The method of claim 1, wherein the antisense oligomer is specifically targeted to an AUG start site of the CYP3A5 mRNA.

11. The method of claim 1, wherein the antisense oligomer is specifically targeted to a G4 structure of the CYP3A5 mRNA.

12. The method of claim 1, wherein the antisense oligomer is 100% complementary to the CYP3A5 mRNA.

13. The method of claim 12, wherein the antisense oligomer is 100% complementary to a region of the CYP3A5 mRNA containing the AUG start codon.

14. The method of claim 12, wherein the antisense oligomer is 100% complementary to a region of the CYP3A5 mRNA containing a G4 structure.

15. A method of treating hypertension in a subject, comprising administering to the subject a non-naturally occurring antisense oligomer specifically targeted to cytochrome CYP3A5 mRNA and effective to reduce expression of cytochrome CYP3A5 enzyme, wherein the subject has a systolic blood pressure of greater than 140 mm Hg, a diastolic blood pressure of greater than 90 mm Hg, and a homozygous CYP3A5*1/*1 genotype, thereby treating hypertension in the subject.

\* \* \* \* \*

SEQUENCE LISTING

<160> NUMBER OF SEQ ID NOS: 19

<210> SEQ ID NO 1
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 1
tttcccatga ggtccatcgc cac          23

<210> SEQ ID NO 2
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 2
cagggaagag atattgaaag ac           22

<210> SEQ ID NO 3
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 3
cagggaagag atactgaaag ac           22

<210> SEQ ID NO 4
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 4
ccgattctgc agctggagcc acac          24

<210> SEQ ID NO 5
<211> LENGTH: 22

```
<212> TYPE: DNA
<213> ORGANISM: Artificial sequence
<220> FEATURE:
<223> OTHER INFORMATION: Synthetic oligonucleotide

<400> SEQUENCE: 5
gagttgacct tcatacgttc tg                                          22

<210> SEQ ID NO 6
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 6
ttgaccttca tacgttctgt gtggg                                       25

<210> SEQ ID NO 7
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 7
acgttctgtg tggggacaac gg                                          22

<210> SEQ ID NO 8
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 8
caaaaaatgg atgcttaccc ttcga                                       25

<210> SEQ ID NO 9
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 9
actccatcgt tcagctctga                                             20

<210> SEQ ID NO 10
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 10
aaatttggcg gtggaaac                                               18

<210> SEQ ID NO 11
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 11
```

```
gacaggcttg cctttctctg                                                 20
```

<210> SEQ ID NO 12
<211> LENGTH: 2006
<212> TYPE: DNA
<213> ORGANISM: Homo sapiens
<400> SEQUENCE: 12

```
ggtctctgga aatttgacac agagtgctat aaaaagtatg gaaaaatgtg ggggtgagta     60
ttctgaaaac ctccattgga tagacctgct actgtgagga ggttacccca ctgcaggata    120
gtctctgccc aggtcttcat gggatgaagc tcttgtcaac ctaaatacaa acagagagag    180
gttctctgaa agaagaggat aattacttgg gagtagaaat tgcaatggga atctgcttgc    240
cgttataaac tatgtgcaaa ttcagggagg taaacaagac aaagatgctc catagaaaat    300
atgagaagaa tctcataact gttttgagat aattattgtt agctacaaag atcaataaca    360
agggtgatgc cacaccaagg ttggacaggc agttgctgga caggtgtcct tgcagaaata    420
ttttttgtgta aagttgaaat agcctttgtg caaagttgtg gttttttgtag acacttttgt    480
aatagttttg tttccaggaa cacaagcata agaatcctct cttcatagcc ttcttgggat    540
ttatttgtca gggttaaaaa acaattagtg acatcacttt ggttctgata agttcacac     600
tcgctattgt aaaactttc gaggcttgtc ctaccaagga tcccatgtgt caccaggtat    660
cgaggtcttc agtctgaact aggctaggag cattgtggtt accactttc tgcaggtttt    720
ggtggcccag ggactcccag catcgccttc tgtccagtgt ctgcctattc ccctcttctt    780
tttttcttcc ttaggtgccc ttttatcaca tgcattgtct cagacccttc taatatgtgc    840
tcataaatgc atggcatcat ctccttccca cattgattca ctttcaatta aaagccaaaa    900
ctccttcatt tagactgaat ttaacatgtg cttttgaaag aagggttgag agataataga    960
gaaacagatt gggaaaccac ttatgctcca cttttttaaa cttttctctgc aagtatggaa   1020
ttttttgttc tgctttgttg tttaaattta agccaaaact tcttaataga aggatataca   1080
aatatttatt ggtttatacc attgcactta ctttgaagaa gagatgctga atattattaa   1140
accattgtgt tccctggtgg gctgatggac tgtgatttta taaggtggtc tcagccaatt   1200
gcagcagctg ttccctgtca gaggggctag aggtttggtg agagcagtgg atgaggtgca   1260
gtggtgtgtt tgttcactag aagcaagtgg gagaaagctt tgcctctttg tacttcttca   1320
tcttctcccc tcaagtcctc agaatccaca gcgctgactg tggagtgctg tggagctggc   1380
atggcccata caggcaacat gacttagtag acagatgaca cagctctaga tgtccatggg   1440
ccccacacca actgcccttg cagcatttag tccttgtgag cacttgatga tttacctgcc   1500
ttcaattttt cactgaccta atattctttt tgataatgaa gtattttaaa catataaaac   1560
attatggaga gtggcatagg agatacccac gtatgtacca cccagcttaa cgaatgctct   1620
actgtcattt ctaaccataa tctctttaaa gagctctttt gtctttcagt atctcttccc   1680
tgtttggacc acattaccct tcatcatatg aagccttggg tggctcctgt gtgagactct   1740
tgctgtgtgt cacaccctaa tgaactagaa cctaaggttg ctgtgtgtcg tacaactagg   1800
ggtatggatt acataacata atgatcaaag tctggcttcc tgggtgtggc tccagctgca   1860
gaatcgggct agtgaagttt aatcagctcc gttgtcccca cacagaacgt atgaaggtca   1920
actccctgtg ctggccatca cagatcccga cgtgatcaga acagtgctag tgaaagaatg   1980
ttattctgtc ttcacaaatc gaaggg                                        2006
```

<210> SEQ ID NO 13
<211> LENGTH: 2006
<212> TYPE: DNA
<213> ORGANISM: Pan troglodytes

<400> SEQUENCE: 13

```
ggtctctgga aatttgacac agagtgctat aaaaagtatg ggaaaatgtg ggggtgagta      60
ttctggaaac ctccattgga tagacctgct actgtgagga ggttacccca ctgcaggata     120
gtctctgccc aggtcttcat gggatgaagc tcttgtcaac ctaaatacaa acagagagag     180
gttgtctgaa agaagaggat aattacttgg gagtagaata ttgcaatggg aatctgcttg     240
ccgttataaa ctatgtgcaa attcagggag gtaaacaaga caaagatgct ccatagaaaa     300
tatgagaaga atctcataac tgttttgaga taattattgt tagctacaaa gatcaataac     360
aagggtgatg ccacaccaag gttggacagg cagttgctgg acaggtgtcc ttgcagaaat     420
atttttgtgt aaagttgaaa tagcctttgt gcaaagttgt ggttttgta gagacttttg      480
taatagtttt gtttccagaa acacaagcat aagaatcctc tcttcatagc cttcttggga     540
tttatttgtc agggttaaaa acaattagt gacgtcactt tggttctgat aaagttcaca      600
ctcgctattg taaaactttt cgaggcttgt cctaccaagg atcccatgtg tcaccaggta     660
tcgaggtctt cagtctgaac taggctggga gcattgtggt taccactttt ctgcaggttt     720
tggtggccca gggactccca gcatcgcctt ctgtccagtg tctgcctatt ccctcttct      780
ttttttcttc cttaggcgcc cttttatcac atgcattgtc tcagacccctt ctaatatgtg    840
ctcataaatt catggcatca tctccttccc acatcgattc actttcaatt aaaagccaaa     900
agtccttcat ttagactgaa tttaacatgt gcttttgaaa gaagggttga gagataatag     960
agaaacagat tgggaaacca cttatgctcc actttttttaa actttctctg caagtatgga    1020
attttttgtt ctgctttgtt gtttaaattt aagccaaaac ttttttaatag aaggatatac    1080
aaatatttat tggtttatac cattgcactt actttgaaga agagatgctg aatattatta    1140
aaccattgtg ttccctggtg ggctgatgga ctgtgatttt ataaggtggt ctcagccaat    1200
tgcagcagct gttccctgtc agagggggcta gaggtttggt gagagcagtg gatgaggtgc    1260
agtggtgtgt ttgttcacta gaggcaagtg ggagaaagct ttgcctcttt gtacttcttc    1320
atcttctccc ctcaagtcct cagaatccac agcgctggct gtggagtgct gtggagctgg    1380
catgccccat acaggcaaca tgacttagta gacagatgac acagctctag atgtccatgg    1440
gccccacacc aactgcccctt gcagcattta gtccttgtga gcatttgatg atttacctgc    1500
cttcaatttt tcactgatct aatattcttt ttgataatga agtattttaa acatataaaa    1560
cattatggag agtggcatag gagatatccca cgtatgcacc acccagctta acgaatgctc    1620
tactgtcatt tctaaccata atctctttaa agagctcttt tgtctttcaa tatctcttcc    1680
ctgtttggac cacattgccc ttcatcacat gaagacttgg gtggctcctg tgtcagactc    1740
ttgctgtgtg tcacacccta atgaactaga acctaaggtt gctgtgtgtc gtacaactag    1800
gggtatggat tacataacat aatgatcaaa gtctggcttc ctgggtgtgg ctccagctgc    1860
agaatcgggc tagtgaagtt taatcagctc cgttgtcccc acacagaatg tatgatggtc    1920
aactccctgt gctggccatc acagatcccg acatgatcag aacagtgcta gtgaaagaat    1980
gttattctgt cttcacaaat cgaagg                                         2006
```

<210> SEQ ID NO 14
<211> LENGTH: 1967
<212> TYPE: DNA

<213> ORGANISM: Callithrix jacchus

<400> SEQUENCE: 14

```
ggtatctgga aatttgactc agaatgtcat aagaagtatg gaaaaatgtg ggggtgagta        60
ttctggaaac ctccattgga tagatctgct tctgtgatga ggttacccca ctgcatagag       120
gatagcctct gtccagggct tcatgggatg aagctcttgt caacctaaat acaaacagag       180
agaggttctc tgaaagaaga cgataattac ttagagtatt gcaatgggag tctgcgtgcc       240
gtttgcaaat tcagggaggt aaagcaagac acagatgctc catatgagga ggatttcata       300
actgttttga gataattact gttagttgca aagatcaata acaaggatga tgccacacaa       360
aggttgaaca ggcagttgct aggcaggtgt ccttgcagaa acattttttgt gtaaaggttg       420
aaatggcctt tgtgcaaagt tgtgtctttt gtagagtctt gtgatagttt tgttactaga       480
aacacaagca tgagaatcct ctcttcagag ccttcttggg atttctcagg gtttaaaaaa       540
tagtgacgtc accttgcttc tgacaacgtt cacactcgct attgtaacat tttcaaggct       600
tgtcctacca aggatccgtg tcaccaggtg tcgggctctt cagtctgaac taggctggga       660
gcattgtggt tacaactctt ctccaggctt tgttggctca gggactccca gcgttgcctt       720
ctgtccagtg gctgcctatt cccctttttcc ttttttccttc cttaggtgcc cgtttatcac       780
atgcattgtt tcagactcct ctaatatgtg ctcataaatg catgacatca tctccttccc       840
acatggactc acttccaatt aaaagcctaa acccttcat ttagacatgg gatttaacag        900
gtgctttta aagaagagtt gagagataac agggaaatag attggaaaac catttatgtt       960
ccacctttttt aaacttcctc ttcaagtatg gaatttttgg ttccactttg ctttttaaat      1020
ttaagccaag actttttaat agaaggatat acaagtactt actggtttat accatcttgc      1080
ttactttgaa gaagagatgc tgaatattct taaaccactg tgttccctgg gggcagatgg      1140
actgatttta tcaggtggcc tcagccaatt gcagcagctg ttccctgtca gaggtgctag      1200
cggtttggtg agagcagtgg aggaggtgcg ctggtgtttg ttcactagaa gcaagtggga      1260
gaagcttttg cctctgtgct tcttcatctt ctctcaccaa gtcctcagaa accacagtgc      1320
cggctgcggg gtgctgtgga gctggcaccg cccatccagg caacatgact gagtagaaac      1380
aacacacagc tcaggatgtc catgggccca caccaactgc cccttgcaac atttactctt      1440
gtaatcatct gatgattaac ctgccttcaa tttttcatgg aaataatatt cttttttgata      1500
ataaaatatt ttaaacatag gaaacattat ggggagtggc ataggaaata cccatgaacg      1560
caccacccag cttaacaaat gctctcctgt catttctaac catgatctct ttcaagagct      1620
cttttgtctt tcaacgtccc ttccttgttt gagccacatt acccttcact gtatgaagac      1680
ttgggtggct cctgtgtcag actcctgctg tttgtcatac cctaatgaac tagaacctaa      1740
ggttgctgtg tattgtacaa ctaggggtat ggattgcata acatcaggat cagtctggct      1800
tcctgggtgt ggctccagat acagaatcgg gctagtgaag cttaatccac tctgttgtcc      1860
ccacgcagat catacgatgg tcaactccct gtgctggcca tcacagaccc cgacataatc      1920
aaagcagtgc tagtgaaaga atgttattcc gtcttcacaa accggag                   1967
```

<210> SEQ ID NO 15
<211> LENGTH: 1998
<212> TYPE: DNA
<213> ORGANISM: Macaca mulatta

<400> SEQUENCE: 15

```
ggtctctgga aatttgacac agaatgttat aaaaagtatg ggaaaatgtg gaggtgagta        60
```

```
ctctggaaac ctccattggg tagaactgct gccgtgatga ggttaccac tgcaaagagg       120
atagtctctg cccagggctt catgggatga agctcttgcc aacccaaata agagagaggt      180
tctctgaaag aagagggtaa ttatttggga gtagaatatt gcagtgggaa tctgcttgcc      240
attataaatg atgtgcaaat tcagggaggt aaacaagaca aagatgctcc aaggaaaatg     300
tgaggagaat ctcataactg ttttgaggta attattatta gctacaaaga ttaataacaa      360
ggatgacgcc acaccaaggt tggacaggca gttgctgggc aggtgtcctt gcagaaatac     420
ttttgtgtaa agttgaaatg actttgtgc aaagttgtgg ttttgtaga acttttgta        480
atagtttgtt tccaggaaca cagcatgaga atcctctctt catagacttc ttgggattta     540
tttgtcaggg ttaaaaaaac aattagtgac atcactttgg ttctgataat gttcacactc     600
gctattgtaa aacttttcga ggcttgtcct accaaggatc ccatgtgtca ccaggtgtcg     660
aggtcttcaa tctgaactag ctgggagca ttgttgtaac cacttttctc caggctttgg     720
gggcccaggg actcccagca tcgccttctg tccagtgtct gcctatcccc ctcttctttt    780
tttcttcctt aggtgcccct ttatcacatg tgttgtctct gacccttcta atatgtgctc    840
ataaatgcat ggcatcatct ccttcccata tcgattcact ttcatttaaa agccaaaact    900
cttctcattta gactttgaat ctaacatgct tttgaaagaa gggttgagaa atagtagaga    960
aacagatttg gaaaccattt atgctcccct ttttaaaact ttctctgcaa gtatggaact   1020
ttttgttctg ctttgttgtt taaatttaag ccaagacttt ttaatggaag gatatacaag    1080
tattattgg ttcataccat tttgcttact ttgaagaaga aatgctgaat attcttaaac    1140
cattgtgttc cctggtgggc tgatgggctg tgattttata aggtgacctc agccaactgc    1200
agcagctgtt ccctgtcgtc agggctagag ttttggtgag agcagtggaa gaggtgcagt    1260
ggtgtgttcg ttcactagaa gcaagcgaga gaaggctttg cctcttgta tttcttcatg      1320
ttctctcatc aagtcctcag aaactgcagc gctggctgca gggtgctgtg gaggtggcac    1380
agcccataca ggcaacacga ctgagcagaa agaacacaca gctctggatg tccgtggtcc    1440
ccacaccaac tgccccttgc aacatttact cttttgagca tctaatgatt tacctgcctt    1500
caattttttca ctgacctaat gttattgata atgaagtatt ttaaacatat aaaacattat    1560
ggagagtggc ataggaaaca cccatgtatg caccatccag cttaacaaat gctgtactgt    1620
catttctaac catgatgtct ttaaagagct cttttggtctt gcaatgtctc ttccctgttt     1680
gggccacatt accettcatc gtatgaaaac ttgggtggtt cctgtgtcag actcttgctg    1740
cgtgtcacac cgtaatgaac tagaacctaa ggttgctgtg tgttgtacaa ctaggggcat    1800
gggttacatg atcaggatca aagtctggct tcctgggtgt ggctccagct gcagaatcag    1860
gctagtgaag tttaatcagc tctgttgtcc ccacacagaa cgcaagatgg tcaactccct    1920
gtgctgacca tcacagatcc cgagatgatc aaaacagtgc tagtgaaaga atgttattct    1980
gtcttcacaa atcgaagg                                                  1998
```

<210> SEQ ID NO 16
<211> LENGTH: 2026
<212> TYPE: DNA
<213> ORGANISM: Macaca fascicularis

<400> SEQUENCE: 16

```
ttcattctat ttaaaataat aatcaaattg tattttgttt cttctcccag ggtctctgga        60
aatttgacac agaatgttat aaaaagtatg gaaaaatgtg gaggtgagta ctctggaaac      120
```

```
ctccattggg tagaactgct gccgtgatga ggttacccac tgcaaagagg atagtctctg      180
cccagggctt catgggatga agctcttgcc aacccaaata agagagaggt tctctgaaag      240
aagagggtaa ttatttggga gtagaatatt gcagtgggaa tctgcttgcc attataaatg      300
atgtgcaaat tcagggaggt aaacaagaca aagatgctcc aaggaaaatg tgaggagaat      360
ctcataactg ttttgaggta attattgtta gctacaaaga ttaataacaa ggatgacacc      420
acaccaaggt tggacaggca gttgctgggc aggtgtcctt gcagaaatac ttttgtgtaa      480
agttgaaatg actttgtgc aaagttgtgg tttttgtaga acttttgta atagtttgtt        540 tccaggaaca cagcatgaga atcctctctt catagacttc ttgggattta tttgtcaggg      600
ttaaaaaaac aattagtgac atcactttgg ttctgataat gttcacactc gctattgtaa      660
aacttttcga ggcttgtcct accaaggatc ccatgtgtca ccaggtgtcg aggtcttcaa      720
tctgaactag gctgggagca ttgttgtaac cacttttctc caggctttgg gggcccaggg      780
actcccagca tcgccttctg tccagtgtct gcctatcccc ctcttctttt tttcttcctt      840
aggtgccctt ttatcacgtg ttgtctctga cccttctaat atgtgctcat aaatgcctgg      900
catcatctcc ttcccatatc gattcacttt catttaaaag ccaaaactct ttcatttaga      960
ctttgaatct aacatgcttt tgaaagaagg gttgagaaat agtagagaaa cagatttgga     1020
aaccatttat gctccccttt ttaaaacttt ctctgcaagt atggaacttt ttgttttgct     1080
ttgctgttta aatttaagcc aagacttttt aatagaagga tatacaagta tttattggtt     1140 cataccatt tgcttacttt gaagaagaaa tgctgaatat tcttaaacca ttgtgttccc      1200
tggtgggctg atgggctgtg attttataag gtgacctcag ccaactgcag cagctgttcc     1260
ctgtcgtcag ggctagagtt ttggtgagag cagtggaaga ggtgcagtgg tgtgttcgtt     1320
cactagaagc aagcgagaga aggctttgcc tctttgtact tcttcatgtt ctctcatcaa     1380
gtcctcagaa actgcagcgc tggctgcagg gtgctgtgga ggtggcacag cccatacagg     1440
caacacgact gagtagaaag aacacacagc tctggatgtc cgtggtcccc acaccaactg     1500 cccccttgcaa catttactct tttgagcata cctgccttca atttttcact gacctaatgt     1560
tattgataat gaagtatttt aaacatataa aacattatgg agagtggcat aggaaacacc     1620
catgtatgca ccatccagct taacaaatgc tgtactgtca tttctaacca tgatgtcttt     1680
aaagagctct ttggtcttgc aatgtctctt ccctgtttgg gccacattac ccttcatcgt     1740
atgaaaactt gggtggttcc tgtgtcagac tcttgctgcg tgtcacaccc taatgaacta     1800
gaacctaagg ttgctgtgtg ttgtacaact aggggcatgg gttacatgat caggatcaaa     1860
gtctggcttc ctgggtgtgg ctccagctgc agaatcaggc tagtgaagtt taatcagctc     1920
tgttgtcccc acacagaacg caagatggtc aactccctgt gctgaccatc acagatcccg     1980
acatgatcaa aacagtgcat gttattctgt cttcacaaat cgaagg                   2026

<210> SEQ ID NO 17
<211> LENGTH: 2334
<212> TYPE: DNA
<213> ORGANISM: Rattus caraco

<400> SEQUENCE: 17
ggcttctggg aatttgacaa atactgccat aaaaaatatg ggaaattatg ggggtaagta       60
ttatagcaaa ttccgctgag tagatttgaa acatttacaa aagtccacag gatgttgagt      120
agaagtgatg tattataaag attcatggag gcttttccta tcaaaggccc catataactt      180
ccagcgtcat gattcacagt tggaatttgg ttaaagaagt tgtatgtttt gatttctca       240
```

```
ggacttgatg actcaggaat ggttcatctg agttttagtt caatatctgg atattctact      300
cttccaatgt tctactctgt gtacctctca ataacatat aatgattccc ctgagacctt       360
taaagatgtg tatctctctg tatttcatat ttagttattt atttatttac aatttgaatc      420
tagtttatgc tttcaagaaa gactgtgagt aatcacaaaa cattgaaaac acatctaggt      480
tttaagaatc catcttctta aagatttttt cacttattca aaaccttcat gatgggaagg      540
ctgctcagta gaaatatgta tgatatgtat gaatatgttc tctgctgatt cttgctgtct      600
tatttggagt cagatgtcct atctaacaca agacagtctt gctagatctt agctgcttaa      660
atatattctg ggggtggagg gaagataatc tttctatata gttgaagctg gccttgaact      720
cctaatcttt ctgcctctac tccttgaatg ctagactttt aataggcaag catacaccat      780
catgttcagc tcatgatact gactttaaaa ttttatttat ttttatttta tgtgtatgag      840
tattttacct gcatgcatat acattcacac acacattgcc atagaggcca agtgtcagat      900
ccattggaac tggagtgaca gacaattgtg aaccaccatg tgggctctgg gaatcaaacc      960
caggacctct ggaagcacaa ccatgatctt aaccattgag tcatctcctc agcccctca      1020 tgatttttta cagtaagtgt gggatatggt cacagcacca tgttccctgc agactaatga    1080 agttttgat cttggaactt ggctagcact tctttcttca tccatcttat ctagtttggt     1140
ggctgtatat gtatgggcca catgtggggc aggctctgaa tgggtgttcc ttctgcctct    1200
gttctacact ttgcctccct atttcctccc aagggtattc ttgttcccct tttaaaggag   1260
tgaagcattc gcattttggt catccttctt gagtttcatg tgttctgtgc atctagggta    1320
atttgagcat ttgggctaat atccacttat caatgagtgc ataccatgtg tgttttttctg   1380 tgattgggtt acctcactca ggatgatatt ttccagttcc atccatttgc ctatgaattt    1440
cataaagtca ttgttttgat agcggaacag tattaattat taataggaga catttaagct    1500
gtgctatgtg actaccttct tctattttct ttgcctatcc ttctagagaa actgttgttc    1560
atactttacc aacgggttct aatgaattct aatgaattat tccatttcag ggccactgga   1620
ggttggttga gaacattgca agaggtgcca ggcgcattgt gctccgtgtt acacacaagt    1680
gaggaggtgt agcctcttca tacctcttta acttctctca cacaccttca gacaactaag   1740
ggctggccac agggtctgct gagtaaacac agcccataca gaccttgtga tcctgctcag   1800
agcacactaa cactgatac cctctggatc atccatttgc acttaaattt ctcacctttg    1860
gttttccact gaatcaatat cctttccgat gatataatat tttgatcaca caaggttatg   1920
aaaatcagtg tgtataggca atattcatgt acgcaccatc caaacttaac aaatgttcaa   1980
atttagtgct aattatcatc tctttgtaga gctattttgt gtttgcctct tcccagcata    2040
ggctatatta cacttcattt cacgagatgc cagtgatcta ggtgttcacg ctgctgtgta   2100
actaggcata ttgttgtgta actaaggtgt gtattatgta atgtctggat cagattctgt    2160
gtttctgggc atgcctccag ctataaaatc cacctggctg ggtttaatcc tctctgcttt    2220
gccaatgcag gttgtacgat ggtcgacagc ctgtgctagc gatcacggat ccagacataa    2280
tcaaaacagt gctggtgaag gaatgttact ctaccttcac aaaccgacgg gtag         2334
```

<210> SEQ ID NO 18
<211> LENGTH: 1996
<212> TYPE: DNA
<213> ORGANISM: Mus musculus

<400> SEQUENCE: 18

```
ggcttctggg aatgtgacat acaatgtcat aaaaaatatg ggaaaatgtg ggggtaagta      60
ttacagcaac ttctactggg tagatttgaa acatttacaa aagctcacag gatcttcagt     120
ggaagcaatg gtattacaaa gatttgtgga ggcttttcct atcaaaggcc ccatatgtct     180
tccagtgtca tgattcacag atggaatttt gttaaaacag ttgcatgttt tgattttctc     240
ctggacttga tggttcagga gtggttcact tgagttagtc cagtgtctgg atattccact     300
cttccaacgt tctcttctgc gtatccctct aataaaatat aacgaatcac tcaagacctt     360
taaatatgtc tctttgtatc tcttatttat ttatttgtac tttagaccaa atttatttaa     420
aaattgaatc taatatgtac tttaaagact atgagctatc acaaaacatt gaaaacacag     480
ctatgttttc aaaatccatc ttctaacaat gtatgtagat ttttatccca ttcaaagtct     540
catgatgcga aggctgctca gtagaaatat gcatgaatat gtcctctatt tactcttgct     600
gtcttatttg tcctggagcc agagtcttat gtgacccaag acagtcttgc tacatattag     660
ctgcttaagt atatcctggg gtggggtggg ggataatctt tctgtatagt tgaagatggc     720
cttgaactcc tgatcattct tcgtctactt cttgaatgct ggaattataa taggcatgca     780
cacaccacca tgtccagctc atgatactga cttaaaaatt ttatttattt ttattttatg     840
catatgagtg tcttacctgc atgcatgtct gtgtaccagg tgcatgcatg cattcattgc     900
cttagaggcc aagtgtcaga tccattggaa ctggagtgac agatagttgt gaaccaccat     960
ggaggctctg ggattcaaac ccaggacctc tgaaatcaca acatgatct taaccaccaa    1020 gtcatcgtct cagctccctc atgatactga ctctttacag taagtgtggg acatagttgc    1080
aggaccatgt tccctgtaga ctaatggagt ttttgatctt ggaacttggt taactgctgc    1140
aaaatgatta tctattatta ataatagtaa ttcttaatag gagacattta agctgtgcta    1200
tgtgatcttc ctctttcttc tttgcttatc tttttttgaaa aactgttgtt catatttcac    1260
caacaaattc tgataaattc taagggccac tggtggttga aacattgca agaggtgtta    1320 gcattgtgtt ctgtgtcaca cacgagcggt gaggcgtggc ctcttcatgt ctctttaact    1380
tctctcacac atctctagat gactacgggc tgaccacagg gtctgttgaa taaatacagc    1440
ccataaagac cttgtgatcc ttctcagagc acacagctta tccatttgca cttaaatttc    1500
tcaccttcgg ttttccatgg acgcaatatc cttttggta atgcaatatt ttgaacatgc    1560
aaaattatga aaactttgt gtgtaggcaa tattcatgca tccactaccc agactttaca    1620
aacgttccaa tttagttcta atcatcttct ctttgtagag ctattttgca tttgcctctt    1680
ccatccatga gctatattac acttcatttc atagaatgcc agagacctgg ggtcagactt    1740
gacctaggtg ctcatgttgc tgtttagcta agcatgttgt tgtataacca aggcaagggt    1800
tatgtaacgt ctggatcaga ttctgagttc ctgggcatgc ttccagctat aaaatccacc    1860
tggttgggtt taatcttttc tgctttgcca atgcaggttg tatgacggtc gacagcctgt    1920
gctggctatc acagatccag acataatcaa aacagtgctg gtgaaggaat gttactctac    1980
cttcacaaac cggcgg                                                   1996

<210> SEQ ID NO 19
<211> LENGTH: 1863
<212> TYPE: DNA
<213> ORGANISM: Danio rerio

<400> SEQUENCE: 19
atgatataaa ttgtggttat gtgtatatga aaatacgaat aacaaatgta gcagggcatt      60
aaattactgt ttattttcttt gcattttaac tttgtgaact ataaactcat gcgtctcctc    120
```

```
atggtttgtg tctcagtttg tgagctaact gtcaacaaca gttattcgct ccacttctcc    180
cctgctggcc acgccactc  ctgcccgatg ctcgcggagc tccacgccca ttaatcatgc    240
atcttttaa  aaaattctga agtagacttt aaccgaaagt gggggtgtc  atggcccttt    300
aaagagtgat agaagtgaga ctttcttttg tccgttcttt tttgagatgt atattgtttt    360
gctattttgt tactgatgac tgctttgcag ctctcagtct tgaattgaat gatttattat    420
agtctttcgt ttgttttgta gcaggaatat tatttattag attgacatgg atataaaaac    480
aatagtgcaa ataaatata  tcttactgta atgcttcatt ttagtttgat gcattgcaaa    540
ccataaattt attttcata  aggtaacaga cttttatag  cagataactt acattcaagc    600
acatttaagg cagcatcata atgagaaatg taattcattt ttactattat tgtaattttc    660
atcattatta atattctata attattagag ttacattttg gaattattgc acacagatat    720
caatctcatc tcagtattag ttagatagtt ctttctgttt ttggttagtc ctaatttatg    780
ttgttttttt atcccttaaa atacaatttg caatggtgct tataaatttt tggtgggtgc    840
tcctaatttt tttctagtat ttctaaattc tttttggttc tcctaaatat ttgaagttgc    900
gagcactgga gctaccaagt aaaaaagtta atttcgagtc ctggtacagc agcgaagttc    960
ctttattata gagtatagtt cctagaaatt ttcagtttta gtacacaatg taactacaaa   1020
agagtcaaac tttaagtggc tggcagctct ctctagaact ctcacatggt cgcccactga   1080
agcgaagtag ggctgtgccc tggatgggag accacatggg aaaactaagt tgctgtcaga   1140
agtggtgtta gtgagaccag caggggcgc  tcattctgca gtctgtgtgg gtcctaaagc   1200
cccagtatag tgaaggggac tctatactgc tcagtgagcg ctgtccttct tcataattgg   1260
cttcatcact ctccaccaat tagctggtgt gtggtgtgcg gtctgacaca atatggctgc   1320
cgtcaatcat cctggtggat gctgcacact ggtggtggat gaggagattg ccccccaaaa   1380
aactgtgcgt agcgctttta gtgtccacaa aaatgatata taaatgtatg gaattattat   1440
tattattacg atgattatta ataaatagga aaataatcta aactctagat gctaatctga   1500
ttcaatgatc tatgctaagc taagctaaaa gtgctcctac aaggacctgg agattggctg   1560
aatggatttt aaaaaatggt aaaacttgtc tgtttaactc taggggggt  tgtaaaatgt   1620
taaaggaaca gattgtaaca aactgtaata ttcatgtcat gattttttg  tttgtattct   1680
tcagattccc atcacatacg atgcattgat gagaatggat tacttggaaa tggccataca   1740
tgaatcaatg cgtgtctttc ctgctggtcc tcgcttagaa agggtctgta aaaagaccgt   1800
agagatcaac ggcattacca taccaaaaaa cacactggtt ggaattcctt tgtatgtttt   1860
aag                                                                 1863
```